(12) United States Patent
Ohlstein et al.

(10) Patent No.: US 9,956,194 B2
(45) Date of Patent: May 1, 2018

(54) COMPOSITIONS AND METHODS OF USING MODIFIED RELEASE SOLABEGRON FOR LOWER URINARY TRACT SYMPTOMS

(71) Applicant: VELICEPT THERAPEUTICS, INC., Malvern, PA (US)

(72) Inventors: Eliot Ohlstein, Glenmoore, PA (US); Raymond E. Stevens, Jr., West Chester, PA (US); H. Jeffrey Wilkins, Sellersville, PA (US)

(73) Assignee: Velicept Therapeutics, Inc., Malvern, PA (US)

( * ) Notice: Subject to any disclaimer, the term of this patent is extended or adjusted under 35 U.S.C. 154(b) by 0 days. days.

(21) Appl. No.: 14/958,610

(22) Filed: Dec. 3, 2015

(65) Prior Publication Data

US 2016/0158176 A1 Jun. 9, 2016

Related U.S. Application Data

(60) Provisional application No. 62/087,021, filed on Dec. 3, 2014.

(51) Int. Cl.
*A61K 31/196* (2006.01)
*A61K 9/00* (2006.01)
(Continued)

(52) U.S. Cl.
CPC .......... *A61K 31/196* (2013.01); *A61K 9/0053* (2013.01); *A61K 9/1676* (2013.01);
(Continued)

(58) Field of Classification Search
CPC .. A61K 9/2081; A61K 9/5078; A61K 9/5084; A61K 9/0053
See application file for complete search history.

(56) References Cited

U.S. PATENT DOCUMENTS 4,478,849 A 10/1984 Ainsworth et al.
4,772,631 A 9/1988 Holloway et al.
(Continued)

FOREIGN PATENT DOCUMENTS

EP 0400519 A 12/1990
EP 0455006 A 11/1991
(Continued)

OTHER PUBLICATIONS

Grudell et al., Dose-response effect of β3-adrenergic receptor agonist, solabegron, on gastrointestinal transit, bowel function, and somatostatin levels in health, Am. J. Physiol. Gastrointest. Live Physiol., vol. 294, Mar. 27, 2008, pp. G1114-G1119.
(Continued)

*Primary Examiner* — Jianfeng Song
(74) *Attorney, Agent, or Firm* — Pepper Hamilton LLP

(57) ABSTRACT

This application relates to pharmaceutical compositions, comprising solabegron that are useful for the treatment of lower urinary tract symptoms such as, for example, overactive bladder and prostate disorders. Additionally, this application relates to methods for treating lower urinary tract symptoms utilizing the pharmaceutical compositions, comprising solabegron. In some embodiments, the pharmaceutical compositions, comprising solabegron comprise a dual release drug delivery system.

60 Claims, 4 Drawing Sheets

(51) Int. Cl.
  *A61K 9/20* (2006.01)
  *A61K 9/24* (2006.01)
  *A61K 45/06* (2006.01)
  *A61K 9/16* (2006.01)
  *A61K 9/50* (2006.01)

(52) U.S. Cl.
  CPC ............ *A61K 9/209* (2013.01); *A61K 9/2077* (2013.01); *A61K 9/2081* (2013.01); *A61K 9/5078* (2013.01); *A61K 9/5084* (2013.01); *A61K 45/06* (2013.01)

(56) References Cited

U.S. PATENT DOCUMENTS

| | | | |
|---|---|---|---|
| 6,069,176 | A | 5/2000 | Tsuchiya et al. |
| 6,123,961 | A | 9/2000 | Aberg |
| 6,251,925 | B1 | 6/2001 | Donaldson et al. |
| 6,395,762 | B1 | 5/2002 | Fobare et al. |
| 6,444,685 | B1 | 9/2002 | Sum |
| 6,451,814 | B1 | 9/2002 | Ashwell et al. |
| 6,548,523 | B2 | 4/2003 | Lawrence et al. |
| 7,022,716 | B2 | 4/2006 | Hu et al. |
| 7,034,053 | B2 | 4/2006 | Deaton et al. |
| 7,425,639 | B2 | 9/2008 | Cooke et al. |
| 7,709,677 | B2 | 5/2010 | Cooke et al. |
| 8,017,613 | B2 | 9/2011 | Scilimati et al. |
| 8,247,415 | B2 | 8/2012 | Berger et al. |
| 8,354,403 | B2 | 1/2013 | Edmondson et al. |
| 8,399,408 | B2 | 3/2013 | Austen et al. |
| 8,642,661 | B2 | 2/2014 | Caltabiano et al. |
| 9,522,129 | B2 | 12/2016 | Caltabiano et al. |
| 2003/0082230 | A1* | 5/2003 | Baichwal ............ A61K 9/2813 424/470 |
| 2004/0122014 | A1 | 6/2004 | Mammen et al. |
| 2005/0101607 | A1 | 5/2005 | Michel et al. |
| 2005/0154041 | A1 | 7/2005 | Michel et al. |
| 2005/0181031 | A1 | 8/2005 | Saito et al. |
| 2005/0261328 | A1 | 11/2005 | Wienrich et al. |
| 2005/0261369 | A1 | 11/2005 | Mehlburger et al. |
| 2006/0084700 | A1 | 4/2006 | Michel |
| 2007/0078181 | A1 | 4/2007 | Michel |
| 2009/0253705 | A1 | 10/2009 | Berger et al. |
| 2010/0240697 | A1 | 9/2010 | Suzuki et al. |
| 2010/0286275 | A1 | 11/2010 | Zhang |
| 2010/0291209 | A1 | 11/2010 | Vergnault et al. |
| 2011/0028461 | A1 | 2/2011 | Berger et al. |
| 2011/0081426 | A1 | 4/2011 | Rao et al. |
| 2012/0035118 | A1 | 2/2012 | Caltabiano et al. |
| 2012/0142725 | A1 | 6/2012 | Van Charldorp et al. |
| 2012/0157432 | A1 | 6/2012 | Edmondson et al. |
| 2012/0202819 | A1 | 8/2012 | Edmondson et al. |
| 2012/0225886 | A1 | 9/2012 | Edmundson et al. |
| 2012/0258963 | A1 | 10/2012 | Berger et al. |
| 2012/0289565 | A1 | 11/2012 | Paborji et al. |
| 2013/0053403 | A1 | 2/2013 | Berger et al. |
| 2013/0172277 | A1 | 7/2013 | Caltabiano et al. |
| 2014/0243544 | A1 | 8/2014 | Wang et al. |
| 2015/0306170 | A1 | 10/2015 | Ahuja et al. |
| 2017/0035716 | A1 | 2/2017 | Ohlstein |
| 2017/0114005 | A1 | 4/2017 | Stevens et al. |
| 2017/0151199 | A1 | 6/2017 | Caltabiano et al. |
| 2017/0348263 | A1 | 12/2017 | Ohlstein et al. |
| 2017/0348288 | A1 | 12/2017 | Ohlstein et al. |

FOREIGN PATENT DOCUMENTS

| | | |
|---|---|---|
| EP | 0543662 A | 5/1993 |
| EP | 0806948 B1 | 9/2000 |
| EP | 1258253 A1 | 11/2002 |
| EP | 1967202 A1 | 9/2008 |
| EP | 2216021 A1 | 8/2010 |
| GB | 940540 | 10/1963 |
| WO | 1995033724 A | 12/1995 |
| WO | 2001042195 A1 | 6/2001 |
| WO | 2001054728 A1 | 8/2001 |
| WO | 2003024483 A1 | 3/2003 |
| WO | 2004041806 A2 | 5/2004 |
| WO | 2004047838 A2 | 6/2004 |
| WO | 2005065673 A1 | 7/2005 |
| WO | 2005067938 A1 | 7/2005 |
| WO | 2006113649 A1 | 10/2006 |
| WO | 2008121268 A1 | 10/2008 |
| WO | 2009057685 A1 | 5/2009 |
| WO | 2009124167 A1 | 10/2009 |
| WO | 2010118291 A2 | 10/2010 |
| WO | 2011025690 A1 | 3/2011 |
| WO | 2011043942 A1 | 4/2011 |
| WO | 2013119910 A1 | 8/2013 |
| WO | 2014034860 A1 | 3/2014 |
| WO | 2015120110 A2 | 8/2015 |
| WO | 2016004056 A1 | 1/2016 |
| WO | 2016090168 A1 | 6/2016 |
| WO | 2017070689 A2 | 4/2017 |
| WO | 2017210696 A1 | 12/2017 |
| WO | 2017210700 A1 | 12/2017 |

OTHER PUBLICATIONS

Hutchinson et al. "β3-Adrenoceptor regulation and relaxation responses in mouse ileum" 2000, Br. J. Pharmacol. 129:1251-1259.

Vrydag et al. "Do gene polymorphisms alone or in combination affect the function of human β-adrenoceptors?" 2009, Br. J. Pharmacol. 156:127-134.

Biers et al., The effects of a new selective β$_3$-adrenoceptor agonist (GW427353) on spontaneous activity and detrusor relaxation in human bladder, *Journal Compilation*, 2006 BJU International (2006), 98:1310-1314.

Irwin et al., Prevalence, Severity, and Symptom Bother of Lower Urinary Tract Symptoms among Men in the EPIC Study: Impact of Overactive Bladder, *European Urology* (Mar. 3, 2009), 56:14-20.

NCT00501267: "A Study to Test the Interaction of Two Medications for the Treatment of Overactive Bladder" available at https://clinicaltrials.gov/ct2/show/NCT00501267?term=NCT00501267&rank=1 (as retrieved on Feb. 15, 2016).

Ohlstein et al., A Multicenter, Double-blind, Randomized, Placebo-controlled Trial of the β3-Adrenoceptor Agonist Solabegron for Overactive Bladder, *European Urology* (Jun. 5, 2012), 62:834-840.

"Gynecological Urology", Le MA ed. Science Press, Aug. 2009, Edition 1, pp. 323-330.

Abrams et al. "Combination treatment with mirabegron and solifenacin in patients with overaactive bladder (OAB) efficacy results from a phase 2 study (Symphony)" May 4-8, 2013 AUA Annual Meeting, San Diego, CA (abstract only).

Arch et al. "Atypical β0adrenoceptor on brown adipocytes as target for anti-obesity drugs" May 10, 1984, Nature 309:163-165.

Bianchetti et al. "In vitro inhibition of intestinal motiliy by phenylethanolaminotetralines: evidence of atypical β-adrenoceptors in rat colon" Aug. 1990, Br. J. Pharmacol. 100:831-839.

Definition of "compound" and "composition" from the Grant & Hackh's Chemical Dictionary, 1987, McGraw-Hill, Inc., p. 148.

Ellsworth et al. "Solabegron: a Potential Future Addition to the β-3 Adrenoceptor Agonist Armamentarium for the Management of Overacative Bladder" (Mar. 5, 2015) Expert Opinion on Investig. Drugs 24(3):413-419.

Emorine et al. "Molecular characterization of the human beta 3-adrenergic receptor" Sep. 8, 1989, Science 245(4922):1118-1121.

Gillespie et al. "Modulation of non-voiding activity by the muscarinergic antagonist tolterodine and the Beta-3-adrenoceptor agonist mirabegron in conscious rats with partial outflow obstruction" 2012, BJU International 110:E132-E142.

Hertzberg et al. "Synthesis of the β3-adrenergic Receptor Agonist Solabegron and Analogous N-(2-ethylamino)-β-amino Alcohols From O-Acylated Cyanohydrins—Expanding the Scope of Minor Enantiomer Recycling" (Feb. 17, 2015) J. Organic Chem. 80(5):2937-2941.

Hicks et al. "GW427353 (solabegron), a novel, selective beta(3)-Adrenergic receptor agonist, evokes blader relaxation and increases

(56) References Cited

OTHER PUBLICATIONS micturition reflex threshold in the dog" Oct. 2007, J. of Pharmacol. and Experimental Therap. 323(1):202-209 (XP000002658787, ISSN: 002-3565).
International Search Report and Written Opinion for PCTEP2005000025 dated May 19, 2005.
International Search Report and Written Opinion for PCT/US2011/046208 dated Sep. 26, 2011.
International Search Report and Written Opinion for PCT/US2013/025285 dated Mar. 25, 2013.
International Search Report and Written Opinion for PCT/US2015/063795 dated Feb. 11, 2016.
International Search Report and Written Opinon for PCT/US2015/038583 dated Sep. 17, 2015.
International Search Report and Written Opinon for PCT/US2016/058516 dated Jun. 5, 2017.
Otsuka et al. "Combination Effect of B3-Adrenoceptor Agonist and Muscarinic Receptor Antagonist on Human Detrusor Muscle Relaxation in Vitro" Oct. 2012, International Continence Society Meeting, pp. 894-895.
Product Label for Myrbetriq™ (mirabegron) Jun. 2012.
Product Label for VESIcare™ (solifenacin succinate) Apr. 2010.
Rackley et al. "Nighttime Dosing with Tolterodine Reduces Overactive Bladder-Related Nocturnal Micturitions in Patients with Overactive Bladder and Nocturia" 2006, Urology 67:731-736.
Singapore Search Report for SG 11201404776P dated Jul. 8, 2015.
Clinical Trials.gov "Alternating Thalidomide and Lenalidomide Plus Rituximab as Initial Treatment for CLL" NCT01779167 May 17, 2010 (retrieved on Aug. 12, 2017). Retrieved from the internet; URL: < https://clinicaltrials.gov/archive/NCT0112,5176/2010_05_17> pp. 1-4; p. 1, brief summary and detailed description.
Lee, J et al.) "Effects of Food Intake on the Pharmacokinetic Properties of Mirabegron Oral 5, 10-18 Controlled-Absorption System: A Single Dose, Randomized, Crossover Study in Healthy Adults" Clinical Therapeutics 2013, vol. 35, No. 3, pp. 333-341; pp. 334, left column, second-third paragraphs; p. 335, left column, third paragraph; p. 337.
Clinical Trials.gov, "Thalidomide, Lenalidomide, and Rituximab for Previously Treated Waldenstrom Macroglobulinemia" NCT01779167, May 26, 2017 (retrieved Sep. 5, 2017 from URL: https://clinicaltrials.gov/archive/NCT01779167/2017_05_26.
International International Search Report and Written Opinon for PCT/US2017/036016 dated Aug. 28, 2017.
International International Search Report and Written Opinon for PCT/US2017/036005 dated Aug. 29, 2017.
Chapple, Christopher R., et al. "A proof-of-concept study: Mirabegron, a new therapy for overactive bladder." Neurourology and urodynamics 32.8 (2013): 1116-1122.
Nitti, V. W., et al. "Mirabegron for the treatment of overactive bladder: a prespecified pooled efficacy analysis and pooled safety analysis of three randomised, double-blind, placebo-controlled, phase III studies." International journal of clinical practice 67.7 (2013): 619-632.
Michel MC. Do β-adrenoceptor agonists induce homologous or heterologous desensitization in rat urinary bladder? Naunyn Schmiedebergs Arch Pharmacol. 2014. 387:215-24.
Chapple, Christopher R., et al. "A phase II dose-ranging study of mirabegron in patients with overactive bladder," Int Urogynecol J (Mar. 8, 2013), 24:1447-1458.

* cited by examiner

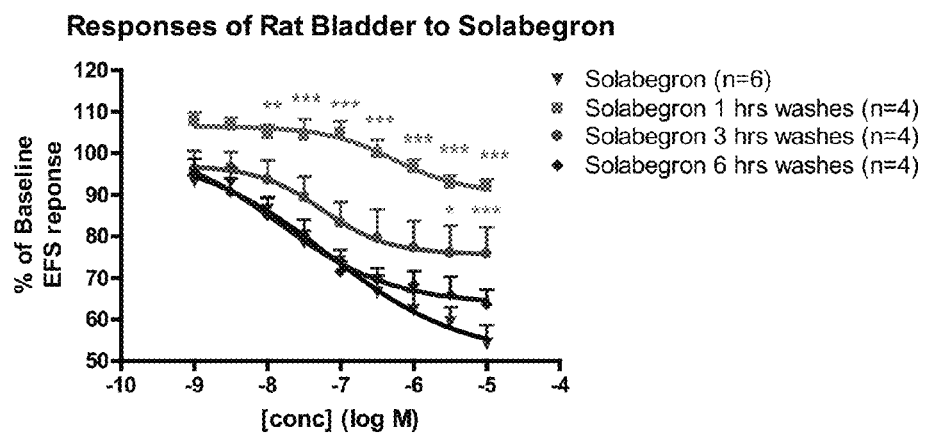

FIGURE 2: Cumulative concentration response curves (CCRC) to solabegron performed after a one hr incubation to the $EC_{90}$ concentration of solabegron and a period of washout using PSS. Two-way ANOVA to compare the curves gives $p<0.001$, with a Bonferroni post hoc test to compare individual points with comparable points on the vehicle incubation curve (black triangles). *=$p<0.05$, =$p<0.01$, *=$p<0.001$

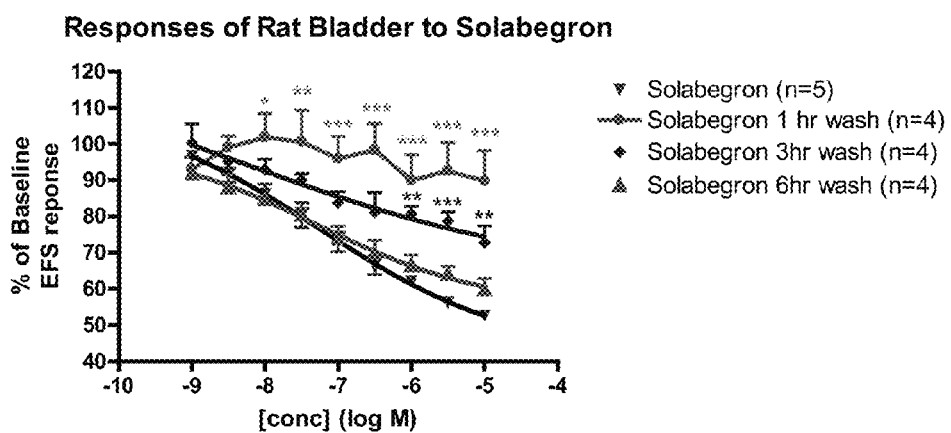

FIGURE 3: Cumulative concentration response curves (CCRC) to solabegron performed after a three hr incubation to the $EC_{90}$ concentration of solabegron and a period of washout using PSS. Two-way ANOVA to compare the curves gives $p<0.001$, with a Bonferroni post hoc test to compare individual points with comparable points on the vehicle incubation curve (black triangles). *=$p<0.05$, =$p<0.01$, *=$p<0.001$

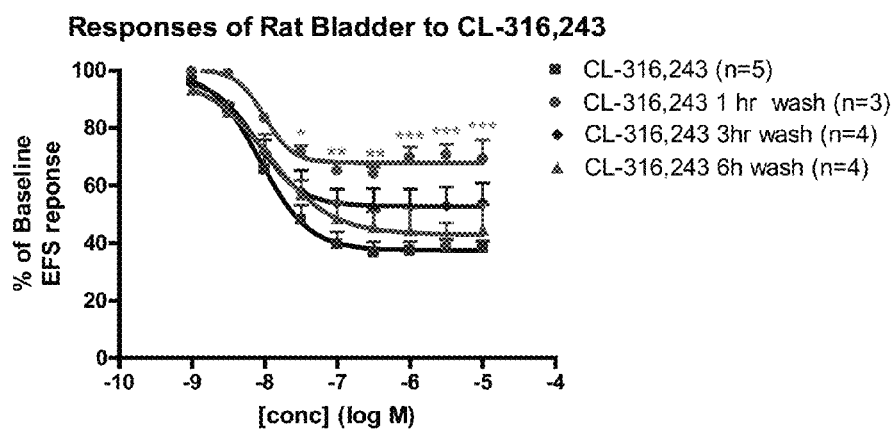

FIGURE 4: Cumulative concentration response curves (CCRC) to CL-316,243 performed after a three hr incubation to the $EC_{90}$ concentration of CL-316,243 and a period of washout using PSS. Two-way ANOVA to compare the curves gives $p<0.001$, with a Bonferroni post hoc test to compare individual points with comparable points on the vehicle incubation curve (black triangles). *=$p<0.05$, =$p<0.01$, *=$p<0.001$

COMPOSITIONS AND METHODS OF USING MODIFIED RELEASE SOLABEGRON FOR LOWER URINARY TRACT SYMPTOMS

This application is a utility patent application claiming domestic priority under 35 U.S.C. § 119(e) to U.S. Provisional Patent Application No. 62/087,021, COMPOSITIONS AND METHODS OF USING MODIFIED RELEASE SOLABEGRON FOR LOWER URINARY TRACT SYMPTOMS, filed Dec. 3, 2014 the disclosure of which is incorporated by reference in its entirety and for all purposes.

SUMMARY

Embodiments of the present application relate to pharmaceutical compositions comprising a therapeutically effective amount of solabegron that achieves a first target $C_{max}$ of solabegron, a second target $C_{max}$ of solabegron, a first target $C_{min}$ of solabegron between the first target $C_{max}$ and the second target $C_{max}$ and a second $C_{min}$ of solabegron after the second target $C_{max}$. In embodiments, the pharmaceutical compositions reduce desensitization of the beta-3 adrenoceptor, particularly when compared to an immediate release formulation of solabegron that may be given, for example, twice daily. In embodiments, the pharmaceutical compositions achieve a plasma concentration [C] of solabegron of about 1 µg/ml or below for a period of time of about 6 hours to about 9 hours during a 24 hour period. In embodiments, the pharmaceutical compositions achieve an AUC of about 11,000 ng hr/ml to about 30,000 ng hr/ml over a 24 hour period. In embodiments the pharmaceutical compositions are administered once a day to a patient in need thereof.

Further embodiments are directed to the use of such pharmaceutical compositions for the treatment of diseases, including, but not limited to, lower urinary tract symptoms (hereinafter "LUTS"), obesity, type 2 diabetes, heart failure, irritable bowel syndrome and similar gastrointestinal disorders, pre-term labor, depression and anxiety. In embodiments, LUTS may be overactive bladder and/or prostate disorders.

Agonist-induced desensitization of G-protein coupled receptors (GPCRs) of the beta-3 adrenoceptor is not well studied. For many disease processes, GPCR desensitization is thought to contribute to the disease process or limit the effect of therapeutic agents. Prolonged exposure of the receptor system molecule to a drug may result in receptor down-regulation. Down-regulation occurs when there is a decrease in the number of receptor system molecules on the cell, thus decreasing the response to continued administration of the therapeutic agent. In addition, more drug may often be needed over time to achieve the same therapeutic response. Pharmaceutical compositions that increase the therapeutically effective properties of solabegron, while otherwise minimizing such desensitization are described herein.

Solabegron (3'-[(2-{[2R]-2-(3-chlorophenyl)-2-hydroxyethyl]amino}ethyl)amino]biphenyl-3-carboxylic acid) is a beta-3 adrenoceptor agonist, with the following structure:

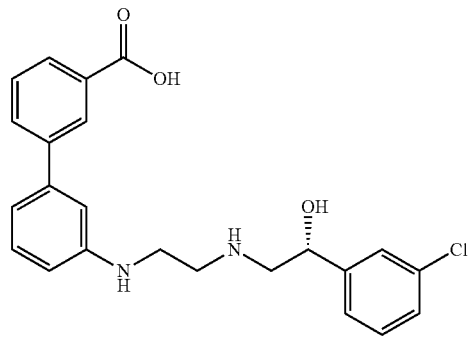 [SMILES: O=C(O)c1cccc(-c2cccc(NCCNC[C@H](O)c3cccc(Cl)c3)c2)c1]

It is further described in U.S. Pat. No. 6,251,925, U.S. Pat. No. 8,642,661 and United States Patent Publication No. 2013/0172277A1 and PCT Application No. US2015/38583 filed Jun. 30, 2015. Solabegron has been demonstrated to significantly reduce the symptoms of overactive bladder (hereinafter "OAB") OAB in women with moderate to severe OAB, showing that solabegron is safe, well-tolerated, and does not demonstrate significant differences in adverse events as compared to placebo.

The question arises whether use of a beta-3 adrenoceptor agonist may be limited by beta-3 receptor desensitization. It is conceivable that like the beta-2 adrenoceptor in airway smooth muscle, continuous, prolonged administration of a beta-3 adrenoceptor agonist will elicit beta-3 receptor desensitization in bladder smooth muscle. Prolonged exposure of a beta-3 adrenoceptor agonist may possibly result in a decrease in the number of beta-3 receptors, a decrease binding affinity or diminish post-receptor signal transduction mechanisms and second messenger signaling, resulting in a diminished therapeutic response.

Embodiments of the present application relate to pharmaceutical compositions comprising a therapeutically effective amount of solabegron that achieves a first target $C_{max}$ of solabegron, a second target $C_{max}$ of solabegron, a first target $C_{min}$ of solabegron between the first target $C_{max}$ and the second target $C_{max}$ and a second $C_{min}$ of solabegron after the second target $C_{max}$. In embodiments, the pharmaceutical composition is a single unit dose. In embodiments, the pharmaceutical composition is two unit doses.

In embodiments, solabegron is solabegron or a pharmaceutically acceptable salt thereof. In embodiments, solabegron is amorphous or the free base. In embodiments, a pharmaceutically acceptable salt thereof may include, but are not limited to, hydrochloride, hydrobromide, hydroiodide, nitrate, sulfate, bisulfate, phosphate, acid phosphate, isonicotinate, acetate, lactate, salicylate, citrate, tartrate, pantothenate, bitartrate, ascorbate, succinate, maleate, gentisinate, fumarate, gluconate, glucaronate, saccharate, formate, benzoate, glutamate, methanesulfonate, ethanesulfonate, benzensulfonate, p-toluenesulfonate and pamoate (i.e., 1,1'-methylene-bis-(2-hydroxy-3-naphthoate)), various amino acids, aluminum, calcium, lithium, magnesium, potassium, sodium, zinc, iron, diethanolamine, amines, such as organic amines, N,N'-dibenzylethylenediamine, chloroprocaine, choline, diethanolamine, dicyclohexylamine, ethylenediamine, N-methylglucamine, and procaine. In embodiments, solabegron is solabegron hydrochloride.

In embodiments, the pharmaceutical composition reduces desensitization of beta-3 adrenoceptor or otherwise increases the therapeutic effect of solabegron, particularly when compared to an immediate release formulation of solabegron that may be given, for examples, twice daily.

Desensitization occurs when the beta-3 adrenoceptor is not otherwise responsive to an agonist (or antagonist), is less responsive to an agonist (or antagonist), or the target tissue (e.g., the bladder) is not otherwise responsive or is less responsive to an agonist (or antagonist).

In embodiments, the pharmaceutical composition achieves a target area under the curve (herein after AUC) of about 11,000 ng hr/ml to about 30,000 ng hr/ml over a 24 hour period. In embodiments, the pharmaceutical composition provides a therapeutic benefit for about 15 to about 22 hours during a 24 hour period. In embodiments, the pharmaceutical composition provides a therapeutic effective [C] for about 15 hours to about 22 hours during a 24 period.

In embodiments, the first target $C_{max}$ is about 1 µg/ml to about 3.5 µg/ml. In embodiments, the first target $C_{max}$ is about 1 µg/ml to about 2 µg/ml. In embodiments, the first target $C_{max}$ is about 1.5 µg/ml to about 3.5 µg/ml. In embodiments, the first target $C_{max}$ is about 1.5 µg/ml to about 3.0 µg/ml. In embodiments, the first target $C_{max}$ is about 2.0 µg/ml to about 3.5 µg/ml. In embodiments, the first target $C_{max}$ is about 2.0 µg/ml to about 3.0 µg/ml.

In embodiments, the first target $C_{min}$ is about 0.25 µg/ml to about 1.5 µg/ml. In embodiments, the first target $C_{min}$ is about 0.25 µg/ml to about 1 µg/ml. In embodiments, the first target $C_{min}$ is about 0.5 µg/ml to about 1.5 µg/ml. In embodiments, the first target $C_{min}$ is about 0.5 µg/ml to about 1.0 µg/ml. In embodiments, the first target $C_{min}$ is about 0.75 µg/ml to about 1.5 µg/ml. In embodiments, the first target $C_{min}$ is about 0.25 µg/ml to about 1.25 µg/ml.

In embodiments, the second target $C_{max}$ is about 1.5 µg/ml to about 4.0 µg/ml. In embodiments, the second target $C_{max}$ is about 1.5 µg/ml to about 3.0 µg/ml. In embodiments, the second target $C_{max}$ is about 2.5 µg/ml to about 4.0 µg/ml. In embodiments, the second target $C_{max}$ is about 2.0 µg/ml to about 4 µg/ml. In embodiments, the second target $C_{max}$ is about 2.0 µg/ml to about 3.0 µg/ml. In embodiments, the second target $C_{max}$ is about 3.0 µg/ml to about 4.0 µg/ml.

In embodiments, the second target $C_{min}$ is about 0.1 µg/ml to about 1.0 µg/ml. In embodiments, the second target $C_{min}$ is about 0.25 µg/ml to about 1.0 µg/ml. In embodiments, the second target $C_{min}$ is about 0.5 µg/ml to about 1.0 µg/ml. In embodiments, the second target $C_{min}$ is about 0.75 µg/ml to about 1.0 µg/ml.

In embodiments, the first $C_{max}$ is achieved at about 0.75 to about 4 hours (i.e., first $T_{max}$) after administration of the pharmaceutical composition. In embodiments, the first $C_{max}$ is achieved at about 1.5 to about 3 hours (i.e., first $T_{max}$) after administration of the pharmaceutical composition.

In embodiments, the first $C_{min}$ is achieved at about 4 to about 8 hours (i.e., first Tmin) after administration of the pharmaceutical composition. In embodiments, the first $C_{min}$ is achieved at about 5 to about 6 hours (i.e., first Tmin) after administration of the pharmaceutical composition.

In embodiments, the time between the first target $C_{max}$ and the second target $C_{max}$ is about 2 to about 8 hours. In embodiments, the time between the first target $C_{max}$ and the second target $C_{max}$ is about 3 to about 7 hours. In embodiments, the time between the first target $C_{max}$ and the second target $C_{max}$ is about 4 to about 6 hours.

In embodiments, the second $C_{max}$ is achieved at about 12 to about 20 hours (i.e., second $T_{max}$) after administration of the pharmaceutical composition. In embodiments, the second $C_{max}$ is achieved at about 14 to about 16 hours (i.e., second $T_{max}$) after administration of the pharmaceutical composition. In embodiments, the second $C_{max}$ is achieved at about 2 to about 8 hours (i.e., second $T_{max}$) after the first $C_{min}$. In embodiments, the second $C_{max}$ is achieved at about 4 to about 6 hours (i.e., second $T_{max}$) after the first $C_{min}$.

In embodiments, the second $C_{min}$ is achieved before about 24 hours (i.e., second $T_{min}$) after administration of the pharmaceutical composition. In embodiments, the second $C_{min}$ is achieved before about 20 hours (i.e., second $T_{min}$) after administration of the pharmaceutical composition. In embodiments, the second $C_{min}$ is achieved before about 16 hours (i.e., second $T_{min}$) after administration of the pharmaceutical composition.

In embodiments, the plasma concentration [C] of solabegron is about 1 µg/ml or below for a period of time of about 6 hours to about 9 hours during a 24 hour period. In embodiments, the plasma concentration [C] of solabegron is about 1 µg/ml or below for a period of time of about 7 hours to about 8 hours during a 24 hour period.

In embodiments, the first $C_{max}$ may be achieved through a first release of solabegron and the second $C_{max}$ may be achieved through a second release of solabegron. In embodiments, the first $C_{max}$ may be achieved during or after a first release of solabegron; that is the first $C_{max}$ may be achieved after the start of the first release. In embodiments, the second $C_{max}$ may be achieved during or after a second release of solabegron; that is the second $C_{max}$ may be achieved after the start of the second release. In embodiments, the first $C_{min}$ may be achieved after the first $C_{max}$ and before the second $C_{max}$. In embodiments, the second $C_{min}$ may be achieved after the second $C_{max}$. In embodiments, the pharmaceutical composition is a single unit dose. In embodiments, the pharmaceutical composition is two unit doses.

In embodiments, the first release of solabegron may be a pulsatile release of solabegron. In embodiments, the second release of solabegron may be a pulsatile release of solabegron. In embodiments, the first release of solabegron may be an immediate release of solabegron. In embodiments, the second release of solabegron may be an immediate release of solabegron. In embodiments, the first release of solabegron may be modified release of solabegron. In embodiments, the second release of solabegron may be a modified release of solabegron. In embodiments, the first release of solabegron may be an extended release of solabegron. In embodiments, the second release of solabegron may be an extended release of solabegron. In embodiments, the first release of solabegron may be a delayed release of solabegron. In embodiments, the second release of solabegron may be a delayed release of solabegron. In embodiments, the first release of solabegron may be a multiparticulate formulation of solabegron. In embodiments, the second release of solabegron may be a multiparticulate formulation of solabegron. In embodiments, the first release of solabegron may be a matrix formulation of solabegron. In embodiments, the second release of solabegron may be a matrix formulation of solabegron. In embodiments, the first and second release of solabegron may be any combination of the foregoing.

In embodiments, the pharmaceutical composition may be a multiparticulate formulation. In embodiments, the multiparticulate formulation may comprise at least two populations of pellets containing solabegron. In embodiments, a first population of pellets is immediate release and a second population is delayed, sustained or modified release. In embodiments, the first population of pellets release the solabegron immediately in the upper GI tract and the second population of pellets release the solabegron later in a lower portion of the GI tract. In embodiments, the second population of pellets that are delayed, sustained or modified release may be coated with a PH dependent coating or a time dependent coating so as to delay the second release of solabegron to the desired position in the GI tract. In embodiments, the pellets may be drug-layered and/or matrix-type pellets.

In embodiments, the pharmaceutical composition may be a drug-coated sphere(s) formulation. In embodiments, the formulation may comprise at least two populations of drug-coated spheres containing solabegron. In embodiments, a first population of drug-coated spheres release the solabegron immediately in the upper GI tract and the second population of drug-coated spheres release the solabegron later in a lower portion of the GI tract. In embodiments, the second population of drug-coated spheres may be coated with a PH dependent coating or a time dependent coating so as to delay the second release of solabegron to the desired position in the GI tract. In embodiments, the pharmaceutical composition is a single unit dose. In embodiments, the pharmaceutical composition is two unit doses.

In embodiments, the pharmaceutical composition may be a bi-layer tablet or a dual-encapsulated capsule. In embodiments, the bi-layer tablet may comprise an immediate release layer and a delayed, sustained or modified release layer. The immediate layer may release solabegron immediately in the GI tract and the modified, delayed or sustained release layer will release solabegron at a later time and lower in the GI tract. The modified release layer may be coated with either a pH dependent coating or a time dependent coating so as to delay the second release of solabegron to the desired position in the GI tract.

In embodiments, the pharmaceutical composition may be a matrix tablet. In embodiments, the matrix tablet may comprise a well-mixed composite of drug(s) with rate-controlling excipients. Numerous sustained and/or delayed release tablets such as membrane controlled system, matrices with water soluble/insoluble polymers, and osmotic systems may be utilized. The tablet may contain either the amorphous form of solabegron or the crystalline form. The delayed/sustained release can be achieved by applying a permeable or semipermeable membrane to the tablet core or by mixing the drug with excipient that is either a hydrophilic polymer with high viscosity and gel forming capability or a hydrophobic excipient that slows down the diffusion of drug molecule. An immediate release drug layer can be coated to the tablet that will be available for an early release in the GI tract, while the delayed release core will be designed to delay the drug release after a time period in a designed region of the GI tract. In embodiments, the pharmaceutical composition is a single unit dose. In embodiments, the pharmaceutical composition is two unit doses.

In embodiments, the pharmaceutical composition may be a multicore tablet. In embodiments the multicore tablet may comprise multiple discrete cores consisting of at least one immediate release core and at least one delayed/sustained release core contained within the same tablet. The at least one immediate release core will be available for an early release in the GI tract, while the at least one delayed/sustained release core will be designed to delay the drug release after a time period in a designed region of the GI tract. In embodiments, the pharmaceutical composition is a single unit dose. In embodiments, the pharmaceutical composition is two unit doses.

In embodiments, the pharmaceutical composition may be a gastroretentive oral delivery system. In embodiments the gastroretentive oral delivery system may comprise a gastroretentive oral dosage form containing solabegron for the multiple releases of solabegron to a patient in need. The formulation will contain a tablet or capsule having both an immediate release and modified release component. The immediate layer will release solabegron immediately in the GI tract, wherein the modified release layer will release solabegron at a later time inside the GI tract. The gastroretentive oral dosage form may utilize mucoadhesive, swellable, high density or floating technologies to prolong residence time in the stomach thereby allowing a prolonged period for release of both first and second releases in the stomach or upper GI. Both releases may contain any physical form of solabegron such as, for example, amorphous or crystalline solid. In embodiments, the pharmaceutical composition is a single unit dose. In embodiments, the pharmaceutical composition is two unit doses.

In embodiments, the first release of solabegron and the second release of solabegron may be identical amounts or may be different amounts of solabegron. In embodiments, the first release of solabegron may be about 75 mg to about 250 mg. In embodiments, the second release of solabegron may be about 100 mg to about 400 mg. In embodiments, the first release and the second release of solabegron may be about 125 mg. In embodiments, the first release and the second release of solabegron may be about 200 mg. In embodiments, the first release of solabegron may be about 125 mg and the second release of solabegron may be about 200 mg. In embodiments the first release of solabegron may be 30, 35, 40, 45, 50, 55, 60, 65, 75, 80, 85, 90, 95, 100, 105, 110, 115, 120, 125, 130, 135, 140, 145, 150, 155, 160, 165, 170, 175, 180, 185, 190, 195, 200, 205, 210, 215, 220, 225, 230, 235, 240, 245, 250, 255, 260, 265, 270, 275, 280, 285, 290, 295, 300, 305, 310, 315, 320, 325, 330, 335, 340, 345, 350, 355, 360, 365, 370, 375, 380, 385, 390, 395, 400, 405, 410, 415, 420, 425, 430, 440, 445, 450, 455, 460, 465, 475, 480, 485, 490, 495 or 500 mg. In embodiments the second release of solabegron may be 30, 35, 40, 45, 50, 55, 60, 65, 75, 80, 85, 90, 95, 100, 105, 110, 115, 120, 125, 130, 135, 140, 145, 150, 155, 160, 165, 170, 175, 180, 185, 190, 195, 200, 205, 210, 215, 220, 225, 230, 235, 240, 245, 250, 255, 260, 265, 270, 275, 280, 285, 290, 295, 300, 305, 310, 315, 320, 325, 330, 335, 340, 345, 350, 355, 360, 365, 370, 375, 380, 385, 390, 395, 400, 405, 410, 415, 420, 425, 430, 440, 445, 450, 455, 460, 465, 475, 480, 485, 490, 495 or 500 mg.

In embodiments, the pharmaceutical composition may further comprise a therapeutically effective amount of one or more additional therapeutic agents. In embodiments, the one or more additional therapeutic agents may be an antimuscarinic agents, alpha adrenoceptor blockers, botulinum toxin, purinergics, cannabinoids, transient receptor potential (TRP) protein inhibitors, prostaglandins, 5-alpha reductase inhibitors, phosphodiesterase-5 inhibitors or percutaneous tibial nerve stimulation. In embodiments, the antimuscarinic agent may be tolterodine, oxybutynin, trospium, solifenacin, darifenacin, propiverine, fesoterodine, and pharmaceutically acceptable salts thereof. In embodiments, alpha adrenoceptor blockers may be tamuslosin, alfuzosin, and silodosin and pharmaceutically acceptable salts thereof. In embodiments, 5-alpha reductase inhibitors may be finasteride, dutaseteride and pharmaceutically acceptable salts thereof. In embodiments, phosphodiesterase-5 inhibitors may be sildenafil, tadalafil, vardenafil, udenafil, avanafil and pharmaceutically acceptable salts thereof.

In embodiments, methods of treating a disease comprising administering to a subject in need thereof a pharmaceutical composition as described herein are provided. In embodiments, the disease may be LUTS, obesity, type 2 diabetes, heart failure, irritable bowel syndrome and similar gastrointestinal disorders, pre-term labor, depression and anxiety, combinations thereof. In embodiments, treating LUTS may include treating or otherwise decreasing frequency of urgency, decreasing nocturia, decreasing urinary micturition frequency, decreasing urinary incontinence, increasing voided volume, decreasing post-void residual volume, and/or improving patient reporting outcomes. In embodiments, the pharmaceutical composition may be administered once a day. In embodiments, the pharmaceutical composition may be administered twice a day.

In embodiments, methods of treating such diseases may further comprise administering a therapeutically effective amount of one or more additional therapeutic agents. In embodiments, the one or more additional therapeutic agents may be administered prior to, simultaneously with, or following the administration of the pharmaceutical composition comprising solabegron. In embodiments, the one or more additional therapeutic agents may be an antimuscarinic agents, alpha adrenoceptor blockers, botulinum toxin, purinergics, cannabinoids, transient receptor potential (TRP) protein inhibitors, prostaglandins, 5-alpha reductase inhibitors, phosphodiesterase-5 inhibitors or percutaneous tibial nerve stimulation. In embodiments, the antimuscarinic agent may be tolterodine, oxybutynin, trospium, solifenacin, darifenacin, propiverine, fesoterodine, and pharmaceutically acceptable salts thereof.

BRIEF DESCRIPTION OF THE FIGURES

FIG. 2—Cumulative Concentration Response Curves (CCRC) to Solabegron Performed After a One Hour Incubation to the $EC_{90}$ Concentration of Solabegron.

FIG. 3—Cumulative Concentration Response Curves (CCRC) to Solabegron Performed After a Three Hour Incubation to the $EC_{90}$ Concentration of Solabegron.

FIG. 4—Cumulative Concentration Response Curves (CCRC) to CL-316,243 Performed After a Three Hour Incubation to the $EC_{90}$ Concentration of CL-316,243.

DETAILED DESCRIPTION

Figure 1:
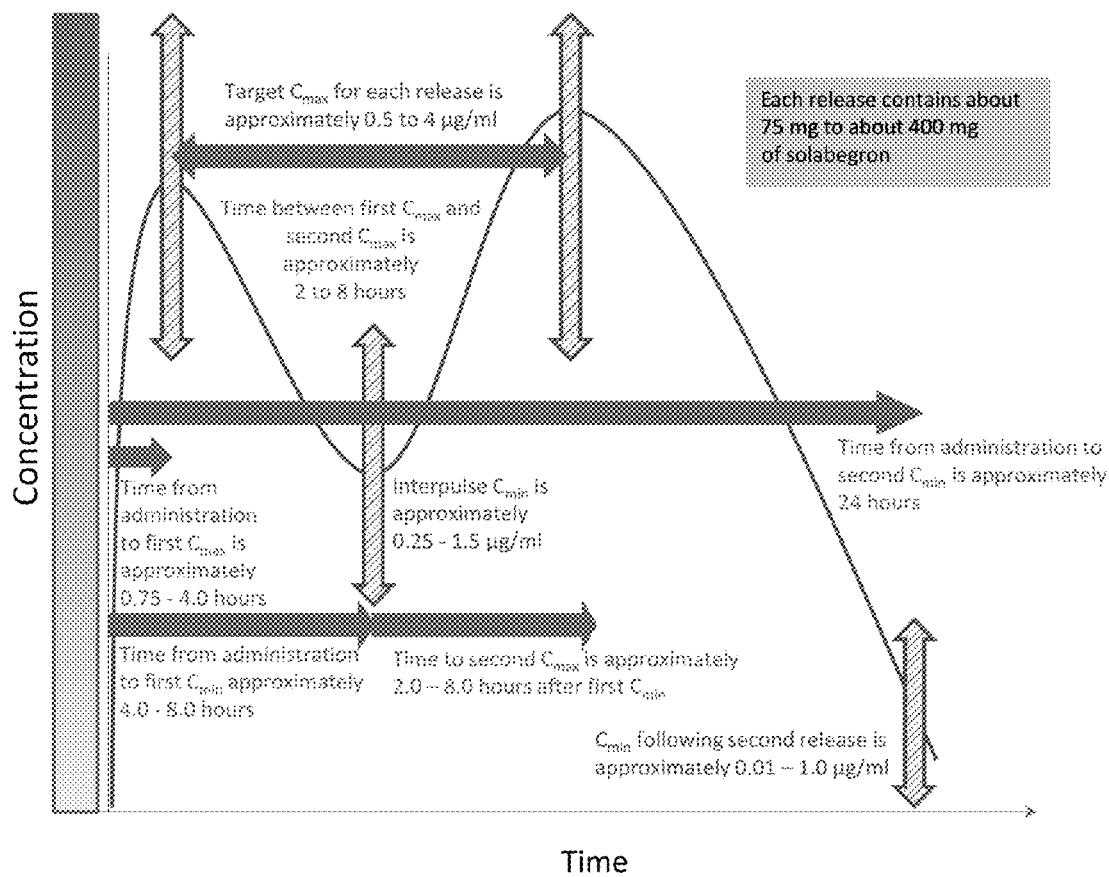
FIG. 1—Graphical Illustration of a Dual-Release Pharmaceutical Composition that Achieves a First Target $C_{max}$, Provides a Period at a First Target $C_{min}$, Achieves a Second Target $C_{max}$, and Finally Provides a Period at a Second Target $C_{min}$.

To prevent or reduce beta-3 adrenoceptor desensitization, it is described herein that the therapeutic administration of a beta-3 adrenoceptor agonist occurs in a manner such that drug occupancy at the receptor occurs at levels that do not elicit significant receptor desensitization and pharmaceutical compositions that achieve the same.

It is well established in the GPCR field that prolonged occupancy of a receptor by an agonist can result in receptor desensitization. A method to limit this is to have the agonist off the receptor, and allow the receptor to recover from agonist occupancy. When examining an entire population of receptors, the entire population of receptors does not need to be unoccupied; fractional occupancy of the entire receptor population can still result in prevention of receptor desensitization and preservation of function. In other words, anything lower than 100% receptor occupancy may still allow some percentage of receptor resensitization.

Certain pharmaceutical compositions and methods of administration as described herein will not produce significant receptor desensitization, while ensuring the method of administration will optimize for the beta-3 adrenoceptor stimulation, thus enabling the target tissue to benefit fully from the administered therapeutic agent. The therapeutic agent, in the present application, is the beta-3 adrenoceptor agonist solabegron and it may be administered in a succession of at least two releases. The releases have a selected amplitude and duration so that the beta-3 adrenoceptor will not down-regulate and the binding affinity of the receptor system molecule will not be diminished.

Embodiments of the present application describe pharmaceutical compositions comprising a therapeutically effective amount of solabegron in a succession of at least two releases, wherein each release is optimized to provide a therapeutically effective plasma concentration [C] that optimizes the tissue response while also providing a lower plasma concentration [C] between the first and second release as well as between the second release and the subsequent administration of the pharmaceutical composition to allow for a sufficient recovery time for the beta-3 adrenoceptors and methods of using the same to treat diseases. An exemplary embodiment of such a pharmaceutical composition and its release profile is provided in (FIG. 1).

Administration of a drug to treat such disease could be by the oral or parenteral routes of administration. For the oral route of administration, a pharmaceutical composition is described that releases drug for systemic absorption at the desired time-points and releases the desired systemic plasma drug levels.

DEFINITIONS

As used herein, the term "about" means plus or minus 10% of a given value. For example, "about 50%" means in the range of 45%-55%.

As used herein the term "agonist" refers to a compound, the presence of which results in a biological activity of a receptor that is the same as the biological activity resulting from the presence of a naturally occurring ligand for the receptor.

The phrase "pharmaceutically acceptable" refers to molecular entities and compositions that are generally regarded as safe and nontoxic. In particular, pharmaceutically acceptable carriers, diluents or other excipients used in the pharmaceutical compositions of this application are physiologically tolerable, compatible with other ingredients, and do not typically produce an allergic or similar untoward reaction (e.g., gastric upset, dizziness and the like) when administered to a patient. Preferably, as used herein, the term "pharmaceutically acceptable" means approved by a regulatory agency of the Federal or a state government or listed in the U.S. Pharmacopoeia or other generally recognized pharmacopoeia for use in animals, and more particularly in humans. The phrase "pharmaceutically acceptable salt(s)", as used herein, includes those salts of compounds of the application that are safe and effective for use in mammals and that possess the desired biological activity. Pharmaceutically acceptable salts include salts of acidic or basic groups present in compounds of the application or in compounds identified pursuant to the methods of the application. Pharmaceutically acceptable acid addition salts include, but are not limited to, hydrochloride, hydrobromide, hydroiodide, nitrate, sulfate, bisulfate, phosphate, acid phosphate, isonicotinate, acetate, lactate, salicylate, citrate, tartrate, pantothenate, bitartrate, ascorbate, succinate, maleate, gentisinate, fumarate, gluconate, glucaronate, saccharate, formate, benzoate, glutamate, methanesulfonate, ethanesulfonate, benzensulfonate, p-toluenesulfonate and pamoate (i.e., 1,1'-methylene-bis-(2-hydroxy-3-naphthoate)) salts. Certain compounds of the application can form pharmaceutically acceptable salts with various amino acids. Suitable base salts include, but are not limited to, aluminum, calcium, lithium, magnesium, potassium, sodium, zinc, iron and diethanolamine salts. Pharmaceutically acceptable base addition salts are also formed with amines, such as organic amines. Examples of suitable amines are N,N'-dibenzylethylenediamine, chloroprocaine, choline, diethanolamine, dicyclohexylamine, ethylenediamine, N-methylglucamine, and procaine.

As used herein the phrase "drug delivery system" refers to any physical form, vehicle or composition that may be formulated by the hand of man to administer a therapeutic agent to a patient in need thereof such as, for example but not limited to the following: tablets, capsules, granules, powders, liquids, suspensions, suppositories, ointments, creams and aerosols.

As used herein the phrase "lower urinary tract symptoms" or "LUTS" refers to a group of medical symptoms comprising increased frequency of urination, increased urinary urgency of urination, painful urination, excessive passage of urine at night (nocturia), poor stream, overactive bladder, hesitancy, terminal dribbling, incomplete voiding, and overflow incontinence.

As used herein the phrase "overactive bladder" or "OAB" refers to a group of medical symptoms comprising urinary urgency, frequent urination, nocturia, urinating unintentionally and urge incontinence.

As used herein, the term "therapeutic" means an agent utilized to treat, combat, ameliorate, protect against or improve an unwanted condition or disease of a subject.

As used herein, the term "effective amount" refers to an amount that results in measurable inhibition of at least one symptom or parameter of a specific disorder or pathological process.

As used herein, the term "desensitization" refers to a state wherein a receptor, specifically in the present application a beta-3 adrenoceptor, has been overexposed to an agonist for an extended period of time and an increased dosage of agonist must be administered to achieve a similar physiological response. It is a process whereby after prolonged agonist exposure, the receptor is uncoupled from its signaling cascade, and thus the biological effect of receptor activation is attenuated.

As used herein the term "therapeutically effective amount" of compositions of the application is a predetermined amount, which confers a therapeutic effect on the treated subject, at a reasonable benefit/risk ratio applicable to any medical treatment. The therapeutic effect may be objective (i.e., measurable by some test or marker) or subjective (i.e., subject gives an indication of or feels an effect or physician observes a change).

As used herein the terms "treat", "treated", or "treating" refer to both therapeutic treatment and prophylactic or preventative measures, wherein the object is to protect against (partially or wholly) or slow down (e.g., lessen or postpone the onset of) an undesired physiological condition, disorder or disease, or to obtain beneficial or desired clinical results such as partial or total restoration or inhibition in decline of a parameter, value, function or result that had or would become abnormal. For the purposes of this application, beneficial or desired clinical results include, but are not limited to, alleviation of symptoms; diminishment of the extent or vigor or rate of development of the condition, disorder or disease; stabilization (i.e., not worsening) of the state of the condition, disorder or disease; delay in onset or slowing of the progression of the condition, disorder or disease; amelioration of the condition, disorder or disease state; and remission (whether partial or total), whether or not it translates to immediate lessening of actual clinical symptoms, or enhancement or improvement of the condition, disorder or disease. Treatment seeks to elicit a clinically significant response without excessive levels of side effects.

As used herein the terms, "release", "releases" "delivery" "pulsatile delivery device" refer to pharmaceutical compositions and methods of treatment wherein a therapeutic agent is delivered rapidly within a short, predetermined period of time, as a result of a biological or external trigger or after a specific lag time.

As used herein the term "immediate release" refers to pharmaceutical compositions that release the active ingredient within a short period of time, typically less than 30 minutes.

As used herein the term "modified release" refers to pharmaceutical compositions that does not otherwise release the active ingredient immediately, for example it may release the active ingredient at a sustained or controlled rate over an extended period of time such as, for example, 4 hours, 8 hours, 12 hours, 16 hours, and 24 hours or release the pharmaceutical dosage after a set time such as, for example, enteric-coated compositions that release the dosage in the intestinal track.

As used herein the terms "QD" and "q.d." mean once a day (from the Latin quaque die).

As used herein the terms "BID" and "b.i.d." mean twice a day (from the Latin bis in die).

As used herein the terms "TID" and t.i.d." mean three times a day (from the Latin ter in die).

As used herein the terms "$C_{max}$", "$C_{min}$", "$T_{max}$" and "$T_{min}$" are terms used in pharmacokinetic analyses of the concentration of a drug against time. $C_{max}$ is a term that refers to the maximum (or peak) plasma concentration that a drug achieves in a specified compartment or test area of the body after the drug has been administrated and prior to the administration of a second dose. $C_{max}$ is the opposite of $C_{min}$, which is the minimum (or trough) concentration that a drug achieves after dosing. $T_{max}$ is the term used in pharmacokinetics to describe the time at which the $C_{max}$ is observed and $T_{min}$ is the term used in pharmacokinetics to describe the time at which the $C_{min}$ is observed after the drug has been administered and prior to the administration of a second dose.

As used herein the terms "area under the curve" and "AUC" is the area under the curve (mathematically known as a definite integral) in a pharmacokinetic plot of the concentration of a drug against time.

EMBODIMENTS

In one embodiment, the present application describes a pharmaceutical composition comprising a therapeutically effective amount of solabegron, wherein the pharmaceutical composition achieves a first target $C_{max}$, a second target $C_{max}$, a first target $C_{min}$ between the first target $C_{max}$ and the second target $C_{max}$, and a second target $C_{min}$ after the second target $C_{max}$. Further embodiments describe pharmaceutical compositions, wherein said pharmaceutical composition achieves a plasma concentration of about 1 µg/ml or less for about 6 hours to about 9 hours during a twenty-four hour period. Further embodiments describe pharmaceutical compositions, wherein said pharmaceutical composition achieves a target AUC of about 11,000 ng·hr/ml to about 30,000 ng·hr/ml over a twenty-four hour period. Further embodiments describe pharmaceutical compositions, wherein the first target $C_{max}$ is achieved after the start of a first release of solabegron and the second target $C_{max}$ is achieved after the start of a second release of solabegron. Further embodiments describe pharmaceutical compositions, wherein said first target $C_{max}$ is about 0.5 µg/ml to about 3.5 µg/ml. Further embodiments describe pharmaceutical compositions, wherein said second target $C_{max}$ is about 1.5 µg·ml to about 4 µg/ml. Further embodiments describe pharmaceutical compositions, wherein said first $C_{min}$ is about 0.25 µg/ml to about 1.5 µg/ml. Further embodiments describe pharmaceutical compositions, wherein said second $C_{min}$ is about 0.01 µg/ml to about 1.0 µg/ml. Further embodiments describe pharmaceutical compositions, wherein the time between the first target $C_{max}$ and the second target $C_{max}$ is about 2 to about 8 hours. Further embodiments describe pharmaceutical compositions, wherein the first $C_{min}$ is achieved at about 4 to about 8 hours after the first administration. Further embodiments describe pharmaceutical compositions, wherein the second $C_{min}$ is achieved before about 24 hours after administration of the pharmaceutical composition. Further embodiments describe pharmaceutical compositions, wherein the first $C_{max}$ is achieved at about 0.75 to about 4 hours after the first administration. Further embodiments describe pharmaceutical compositions, wherein the second $C_{max}$ is achieved at about 2 to about 8 hours after the first $C_{min}$. Further embodiments describe pharmaceutical compositions, wherein the first release comprises about 75 mg to about 400 mg of solabegron. Further embodiments describe pharmaceutical compositions, wherein the second release comprises about 100 mg to about 400 mg of solabegron. Further embodiments describe pharmaceutical compositions, further comprising one or more additional therapeutic agents selected from the group consisting of: antimuscarinic agents; alpha adrenoceptor blockers; botulinum toxin; puringerics; cannabinoids; transient receptor potential (TRP) protein inhibitors; prostaglandins; percutaneous tibial nerve stimulation; 5-alpha reductase inhibitors; and phosphodiesterase-5 inhibitors.

In one embodiment, the present application describes a pharmaceutical composition for the delivery of solabegron, comprising: at least one immediate release composition, comprising solabegron and at least one pharmaceutically acceptable carrier or diluent; and at least one modified release composition, comprising solabegron and at least one pharmaceutically acceptable carrier or diluent. Further embodiments describe pharmaceutical compositions, wherein the at least one immediate release composition comprises about 75 mg to about 400 mg solabegron. Further embodiments describe pharmaceutical compositions, wherein the at least one modified release composition comprises about 100 mg to about 400 mg solabegron. Further embodiments describe pharmaceutical compositions, wherein the at least one immediate release composition achieves a blood plasma $C_{max}$ in about 0.75 to about 4 hours after administration to a patient in need of treatment. Further embodiments describe pharmaceutical compositions, wherein the at least one modified release composition achieves a blood plasma $C_{max}$ in about 2 to about 8 hours after the first $C_{min}$. Further embodiments describe pharmaceutical compositions, further comprising one or more additional therapeutic agents or treatments useful for the treatment of LUTS, obesity, type 2 diabetes, heart failure, irritable bowel syndrome and similar gastrointestinal disorders, pre-term labor, depression and anxiety, wherein the one more additional therapeutic agents or treatments are selected from the groups consisting of: antimuscarinic agents; alpha adrenoceptor blockers; botulinum toxin; puringerics; cannabinoids; transient receptor potential (TRP) protein inhibitors; prostaglandins; percutaneous tibial nerve stimulation; 5-alpha reductase inhibitors; and phosphodiesterase-5 inhibitors. Further embodiments describe pharmaceutical compositions, wherein the one or more additional therapeutic agents may be administered prior to, simultaneously with, or following the administration of the pharmaceutical composition comprising solabegron. Further embodiments describe pharmaceutical compositions, wherein the at least one immediate release composition achieves a blood plasma $C_{max}$ from about 0.5 µg/ml to about 3.5 µg/ml. Further embodiments describe pharmaceutical compositions, wherein the at least one modified release composition achieves a blood plasma $C_{max}$ from about 1.5 µg/ml to about 4 µg/ml. Further embodiments describe pharmaceutical compositions, wherein a $C_{min}$ from about 0.25 µg/ml to about 1.5 µg/ml is achieved in about 4 to about 8 hours after administration to a patient in need of treatment. Further embodiments describe pharmaceutical compositions, wherein a $C_{min}$ from about 0.01 µg/ml to about 1.0 µg/ml is achieved before about 24 hours after administration to a patient in need of treatment. Further embodiments describe pharmaceutical compositions, wherein the first release composition comprises about 125 mg solabegron and the second release composition comprises about 125 mg solabegron. Further embodiments describe pharmaceutical compositions, wherein the first release composition comprises about 200 mg solabegron and the second release composition comprises about 200 mg solabegron. Further embodiments describe pharmaceutical compositions, wherein the first release composition comprises about 125 mg solabegron and the second release composition comprises about 200 mg solabegron.

In one embodiment, the present application describes a pharmaceutical composition comprising a therapeutically effective amount of the amorphous solid form of solabegron, wherein the pharmaceutical composition achieves a first target $C_{max}$, a second target $C_{max}$, a first target $C_{min}$ between the first target $C_{max}$ and the second target $C_{max}$, and a second target $C_{min}$ after the second target $C_{max}$. In one embodiment, the present application describes a pharmaceutical composition comprising a therapeutically effective amount of the hydrochloride salt form of solabegron, wherein the pharmaceutical composition achieves a first target $C_{max}$, a second target $C_{max}$, a first target $C_{min}$ between the first target $C_{max}$ and the second target $C_{max}$, and a second target $C_{min}$ after the second target $C_{max}$. Further embodiments describe pharmaceutical compositions, wherein said pharmaceutical composition achieves a plasma concentration of about 1 µg/ml or less for about 6 hours to about 9 hours during a twenty-four hour period. Further embodiments describe pharmaceutical compositions, wherein said pharmaceutical composition achieves a target AUC of about 11,000 ng·hr/ml to about 30,000 ng·hr/ml. Further embodiments describe pharmaceutical compositions, further comprising two separate and distinct releases of solabegron. Further embodiments describe pharmaceutical compositions, wherein the two release are contained within two separate and distinct drug delivery systems. Further embodiments describe pharmaceutical, wherein the two separate and distinct drug delivery systems are administered BID. Further embodiments describe pharmaceutical compositions, wherein the BID administration is separated by a period of between about 6 to about 18 hours. Further embodiments describe pharmaceutical compositions, wherein the two releases are contained within the same drug delivery system. Further embodiments describe pharmaceutical compositions, wherein the delivery vehicle is selected from the group consisting of: tablets; bi-layer tablets; capsules; multiparticulates; drug coated spheres/pellets; matrix tablets; and multicore tablets. Further embodiments describe pharmaceutical compositions, wherein the first target $C_{max}$ is achieved after the start of a first release of solabegron and the second target $C_{max}$ is achieved after the start of a second release of solabegron. Further embodiments describe pharmaceutical compositions, wherein said first target $C_{max}$ is about 0.5 µg/ml to about 3.5 µg/ml. Further embodiments describe pharmaceutical compositions, wherein said second target $C_{max}$ is about 1.5 µg·ml to about 4 µg/ml. Further embodiments describe pharmaceutical compositions, wherein said first $C_{min}$ is about 0.25 µg/ml to about 1.5 µg/ml. Further embodiments describe pharmaceutical compositions, wherein said second $C_{min}$ is about 0.01 µg/ml to about 1.0 µg/ml. Further embodiments describe pharmaceutical compositions, wherein the time between the first target $C_{max}$ and the second target $C_{max}$ is about 2 to about 8 hours. Further embodiments describe pharmaceutical compositions, wherein the first $C_{min}$ is achieved at about 4 to about 8 hours after the first administration. Further embodiments describe pharmaceutical compositions, wherein the second $C_{min}$ is achieved before about 24 hours after administration of the pharmaceutical composition. Further embodiments describe pharmaceutical compositions, wherein the first $C_{max}$ is achieved at about 0.75 to about 4 hours after the first administration. Further embodiments describe pharmaceutical compositions, wherein the second $C_{max}$ is achieved at about 2 to about 8 hours after the first $C_{min}$. Further embodiments describe pharmaceutical compositions, wherein the first release comprises about 30 mg to about 500 mg of solabegron. Further embodiments describe pharmaceutical compositions, wherein the second release comprises about 30 mg to about 500 mg of solabegron. Further embodiments describe pharmaceutical compositions, further comprising one or more additional therapeutic agents selected from the group consisting of: antimuscarinic agents; alpha adrenoceptor blockers; botulinum toxin; purinergics; cannabinoids; transient receptor potential (TRP) protein inhibitors; prostaglandins; percutaneous tibial nerve stimulation; 5-alpha reductase inhibitors; and phosphodiesterase-5 inhibitors.

In one embodiment the present application describes a pharmaceutical composition comprising a therapeutically effective amount of solabegron, wherein the pharmaceutical composition releases at least two releases of solabegron, wherein a first release of solabegron achieves a first target $C_{max}$, a second release of solabegron achieves a second target $C_{max}$, a first target $C_{min}$ is achieved between the first release and the second release and a second $C_{min}$ is achieved after the second release. Further embodiments of the present application describe pharmaceutical compositions, wherein said first target $C_{max}$ is about 1.5 µg/ml to about 4 µg/ml, wherein said first $C_{min}$ is about 0.5 µg/ml to about 1.5 µg/ml, wherein said second target $C_{max}$ is about 1.5 µg·ml to about 4 µg/ml and wherein said second $C_{min}$ is about 0.01 µg/ml to about 0.5 µg/ml. Other embodiments of the present application describe pharmaceutical, wherein the first $C_{max}$ is achieved at about 1 to about 3 hours after the first release, wherein the first $C_{min}$ is achieved at about 2 to about 4 hours after the first release, wherein the time between the first target $C_{max}$ and the second target $C_{max}$ is about 2 to about 8 hours, wherein the second $C_{max}$ is achieved at about 1 to about 3 hours after the second release and wherein the second $C_{min}$ is achieved at about 3 to about 8 hours after the second release. Further embodiments of the present application describe pharmaceutical compositions, wherein the first release comprises about 100 mg to about 300 mg of solabegron and wherein the second release comprises about 100 mg to about 300 mg of solabegron. Other embodiments of the present application describe pharmaceutical compositions, wherein the concentration of solabegron is about 0.5 µg/ml or below for a period of time from about 12 to about 18 hours. Still other embodiments of the present application describe pharmaceutical compositions, further comprising one or more additional therapeutic agents or treatments useful for the treatment of LUTS, obesity, type 2 diabetes, heart failure, irritable bowel syndrome and similar gastrointestinal disorders, pre-term labor, depression and anxiety, wherein the one more additional therapeutic agents or treatments are antimuscarinic agents, alpha adrenoceptor blockers, botulinum toxin, purinergics, cannabinoids, transient receptor potential (TRP) protein inhibitors, prostaglandins, 5-alpha reductase inhibitors, phosphodiesterase-5 inhibitors or percutaneous tibial nerve stimulation and the one or more additional therapeutic agents may be administered prior to, simultaneously with, or following the administration of the pharmaceutical composition comprising solabegron.

In one embodiment, the present application describes a pharmaceutical composition for the delivery of solabegron, comprising: at least one immediate release composition, comprising solabegron and at least one pharmaceutically acceptable carrier or diluent; and at least one modified release composition, comprising solabegron and at least one pharmaceutically acceptable carrier or diluent. Additional embodiments describe pharmaceutical compositions, wherein the at least one immediate release composition comprises about 100 mg to about 300 mg solabegron and the modified release composition comprises about 100 mg to about 300 mg solabegron. Further embodiments describe pharmaceutical compositions, wherein at least one immediate release composition achieves a blood plasma $C_{max}$ in about 1 to about 3 hours after administration to a patient in need of treatment and at least one modified release composition achieves a blood plasma $C_{max}$ in about 5 to about 11 hours after administration to a patient in need of treatment. Other embodiments describe pharmaceutical compositions, wherein the at least one immediate release composition achieves a blood plasma $C_{max}$ from about 1.5 µg/ml to about 4 µg/ml and the at least one modified release composition achieves a blood plasma $C_{max}$ from about 1.5 µg/ml to about 4 µg/ml. Still additional embodiments describe pharmaceutical compositions, wherein a $C_{min}$ from about 0.5 µg/ml to about 1.5 µg/ml is achieved in about 3 to about 5 hours after administration to a patient in need of treatment and a $C_{min}$ less than about 0.5 µg/ml is achieved after about 12 hours after administration to a patient in need of treatment. Still other embodiments of the present application describe pharmaceutical compositions, further comprising one or more additional therapeutic agents or treatments useful for the treatment of LUTS, obesity, type 2 diabetes, heart failure, irritable bowel syndrome and similar gastrointestinal disorders, pre-term labor, depression and anxiety, wherein the one more additional therapeutic agents or treatments are antimuscarinic agents, alpha adrenoceptor blockers, botulinum toxin, purinergics, cannabinoids, transient receptor potential (TRP) protein inhibitors, prostaglandins, 5-alpha reductase inhibitors, phosphodiesterase-5 inhibitors or percutaneous tibial nerve stimulation and the one or more additional therapeutic agents may be administered prior to, simultaneously with, or following the administration of the pharmaceutical composition comprising solabegron.

In one embodiment the present application describes a pharmaceutical composition for the delivery of solabegron, comprising: at least one immediate release composition, comprising solabegron and at least one pharmaceutically acceptable carrier or diluent; and at least one modified release composition, comprising solabegron and at least one pharmaceutically acceptable carrier or diluent. Further embodiments describe pharmaceutical compositions, wherein the at least one immediate release composition comprises about 75 mg to about 400 mg solabegron. Further embodiments describe pharmaceutical compositions, wherein the at least one modified release composition comprises about 75 mg to about 400 mg solabegron. Further embodiments describe pharmaceutical compositions, wherein the at least one immediate release composition achieves a blood plasma $C_{max}$ in about 0.75 to about 4 hours after administration to a patient in need of treatment. Further embodiments describe pharmaceutical compositions, wherein the at least one modified release composition achieves a blood plasma $C_{max}$ in about 6 to about 16 hours after administration to a patient in need of treatment. Further embodiments describe pharmaceutical compositions, further comprising one or more additional therapeutic agents or treatments useful for the treatment of LUTS, obesity, type 2 diabetes, heart failure, irritable bowel syndrome and similar gastrointestinal disorders, pre-term labor, depression and anxiety, wherein the one more additional therapeutic agents or treatments are selected from the groups consisting of: antimuscarinic agents; alpha adrenoceptor blockers; botulinum toxin; purinergics; cannabinoids; transient receptor potential (TRP) protein inhibitors; prostaglandins; percutaneous tibial nerve stimulation; 5-alpha reductase inhibitors; and phosphodiesterase-5 inhibitors. Further embodiments describe pharmaceutical compositions, wherein the one or more additional therapeutic agents may be administered prior to, simultaneously with, or following the administration of the pharmaceutical composition comprising solabegron. Further embodiments describe pharmaceutical compositions, wherein the at least one immediate release composition achieves a blood plasma $C_{max}$ from about 1.0 µg/ml to about 3.5 µg/ml. Further embodiments describe pharmaceutical compositions, wherein the at least one modified release composition achieves a blood plasma $C_{max}$ from about 1.5 µg/ml to about 4 µg/ml. Further embodiments describe pharmaceutical compositions, wherein a $C_{min}$ from about 0.25 µg/ml to about 1.5 µg/ml is achieved in about 4 to about 8 hours after administration to a patient in need of treatment. Further embodiments describe pharmaceutical compositions, wherein a $C_{min}$ from about 0.1 µg/ml to about 1.0 µg/ml is achieved at about 24 hours after administration to a patient in need of treatment. Further embodiments describe pharmaceutical compositions, wherein the at least one immediate release composition comprises about 125 mg solabegron and the at least one modified release composition comprises about 125 mg solabegron. Further embodiments describe pharmaceutical compositions, wherein the at least one immediate release composition comprises about 200 mg solabegron and the at least one modified release composition comprises about 200 mg solabegron. Further embodiments describe pharmaceutical compositions, wherein the at least one immediate release composition comprises about 125 mg solabegron and the at least one modified release composition comprises about 200 mg solabegron.

The pharmaceutical compositions of the present application can be administered transdermally, orally or parenterally, such as subcutaneously or intravenously, as well as sublingually to various mammalian species known to be subject to such maladies, e.g., humans, in an effective amount up to about 1 gram, preferably up to about 800 mg, more preferably up to about 600 mg in a once-a-day regimen.

The pharmaceutical compositions of the present application can be administered for any of the uses described herein by any suitable means, for example, orally, such as in the form of tablets, capsules, granules or powders; sublingually; bucally; parenterally, such as by subcutaneous, intravenous, intramuscular, or intrasternal injection or infusion techniques (e.g., as sterile injectable aqueous or non-aqueous solutions or suspensions); in dosage unit formulations containing non-toxic, pharmaceutically acceptable vehicles or diluents. The present compositions can, for example, be administered in a form suitable for immediate release or extended release. Immediate release or extended release can be achieved by the use of suitable pharmaceutical compositions comprising the present compounds, or, particularly in the case of extended release, by the use of devices such as subcutaneous implants or osmotic pumps. The present compositions can also be administered liposomally.

The formulation for a beta-3 adrenoceptor agonist can significantly modify the absorption profile. For example, some compounds are differentially absorbed in different regions of the GI tract. Some of the factors involved in absorption can include pH-dependent solubility, particle size, lipophilicity, ionization, GI-motility or transporters. In the current example for the absorption of solabegron, solabegron demonstrates pH-dependent solubility and absorption. Accordingly, solabegron and pharmaceutical salts thereof display the optimum absorption in the proximal GI tract. Pharmaceutical compositions are presented herein that improve the pH-dependent solubility of solabegron in the distal GI tract. Under these improved conditions, a second release of solabegron and absorption will result. Additionally, methods for the release of solabegron in the distal GI tract based on pH are presented herein.

Another example of producing a delayed second release is based on the transit time of the dosage form. This is achievable through the time-dependent erosion of the dosage form coating. The GI transit time is well understood, and the coatings are designed to erode within a specific time range that corresponds to a specific region within the GI tract. Pharmaceutical compositions and methods of use are presented herein for the release of solabegron based on time-dependent erosion.

Exemplary compositions for oral administration include emulsions and suspensions which can contain, for example, microcrystalline cellulose for imparting bulk, alginic acid or sodium alginate as a suspending agent, methylcellulose as a viscosity enhancer, and sweeteners or flavoring agents such as those known in the art; and immediate release tablets which can contain, for example, microcrystalline cellulose, dicalcium phosphate, starch, magnesium stearate and/or lactose and/or other excipients, binders, extenders, disintegrants, diluents and lubricants such as those known in the art. The compositions of the present application can also be delivered through the oral cavity by sublingual and/or buccal administration. Molded tablets, compressed tablets or freeze-dried tablets are exemplary forms which may be used. Exemplary compositions include those formulating the present beta-3 adrenoceptor agonists with fast dissolving diluents such as mannitol, lactose, sucrose and/or cyclodextrins. The compositions of the present application may take the form of pulsatile delivery systems such as, for example, PULSINCAP®, MICROPUMP®, MEDUSA™, PORT® system, CHRONOTROPIC®, TIME CLOCK®, multilayered tablets, DiffuCORE®, rupturable tablets, ACCU- BREAK® system, DIFFUCAPS®, DIFFUTABS®, Eurand MINITABS®, MICROCAPS®, SODAS®, IPDAS®, OsDrC®, OptiDose™, OptiMelt™, ZYDIS®, CODAS®, PRODAS®, TMDS®, DMDS®, PMDS®, GEOCLOCK®, GEOMATRIX®, PULSYS®, OROS® INTELLIMATRIX™ and VERSETROL™. Also included in such formulations may be high molecular weight excipients such as celluloses (avicel) or polyethylene glycols (PEG). Such formulations can also include an excipient to aid mucosal adhesion such as hydroxy propyl cellulose (HPC), hydroxy propyl methyl cellulose (HPMC), sodium carboxy methyl cellulose (SCMC), maleic anhydride copolymer (e.g., Gantrez), and agents to control release such as polyacrylic copolymer (e.g. Carbopol 934). Lubricants, glidants, flavors, coloring agents and stabilizers may also be added for ease of fabrication and use.

The therapeutic agents in the pharmaceutical compositions of the present application may exist in any physical form known to one of skill in the art such as, for example, nanoparticles, crystalline solids, amorphous solids, polymorphs, ionic solids such as, for example, cations, anions and zwitterions, pharmaceutically acceptable salts, hydrates, solvates, stereoisomers, solutions and suspensions. Crystalline solids have regular ordered arrays of components held together by uniform intermolecular forces, whereas the components of amorphous solids are not arranged in regular arrays. Hydrates are substances that incorporate at least one water molecule into their crystalline matrix. Solvates are substances that incorporate at least one solvent molecule into their crystalline matrix. Polymorphs exhibit different crystalline structures for molecules that have the same molecular formula and sequence of bonded atoms. Stereoisomers are isomeric molecules that have the same molecular formula and sequence of bonded atoms (constitution), but that differ only in the three-dimensional orientations of their atoms in space.

Further, the therapeutic agents in the pharmaceutical compositions of the present application may exist in any isotopic form known to one of skill in the art such as, for example, deuterated, tritiated, 13C, 14C, etc.

Exemplary compositions for parenteral administration include injectable solutions or suspensions which can contain, for example, suitable non-toxic, parenterally acceptable diluents or solvents, such as mannitol, 1,3-butanediol, water, polyethylene glycol, Ringer's solution, an isotonic sodium chloride solution, or other suitable dispersing or wetting and suspending agents, including synthetic mono- or diglycerides, and fatty acids, including oleic acid, or Cremaphor.

Exemplary compositions for transdermal administration include transdermal therapeutic systems (hereinafter "TTS"). TTS are patches having a layered structure and comprising at least one active pharmaceutical ingredient in a reservoir layer. A distinction is made between matrix-type and reservoir-type TTS: in the first case the reservoir layer containing the active pharmaceutical ingredient has a pressure-sensitive adhesive finish, and in the second case a membrane which controls the rate of release of the active pharmaceutical ingredient, and where appropriate an additional pressure-sensitive adhesive layer, are present.

Exemplary compositions for delivery directly to the bladder include extended-release solid-drug core devices that are implanted via catheter.

It will be understood that the specific dose level and frequency of dosage for any particular subject can be varied and will depend upon a variety of factors including the activity of the specific beta-3 adrenoceptor agonist employed, the metabolic stability and length of action of that compound, the species, age, body weight, general health, gender and diet of the subject, the mode and time of administration, rate of excretion, drug combination, and severity of the particular condition.

The present application includes within its scope pharmaceutical compositions comprising, as an active ingredient, a therapeutically effective amount of solabegron, alone or in combination with a pharmaceutical carrier or diluent. Optionally, the pharmaceutical compositions of the present invention can be used alone, or in combination with other suitable therapeutic agents or treatments useful in the treatment of LUTS including: antimuscarinic agents, alpha adrenoceptor blockers, botulinum toxin, puringerics, cannabinoids, transient receptor potential (TRP) protein inhibitors, prostaglandins, percutaneous tibial nerve stimulation, 5-alpha reductase inhibitors and phosphodiesterase-5 inhibitors.

Optionally, the pharmaceutical compositions of the present invention can be used alone, or in combination with other suitable therapeutic agents or treatments useful in the treatment of obesity, diabetes, heart failure, irritable bowel syndrome (IBS), preterm labor, anxiety or depression.

Such other therapeutic agent(s) may be administered prior to, simultaneously with, or following the administration of the beta-3 adrenoceptor agonist containing pharmaceutical composition in accordance with the invention.

Examples of suitable antimuscarinic agents for use in combination with the pharmaceutical compositions of the present application include tolterodine, oxybutynin, trospium, solifenacin, darifenacin, propiverine, fesoterodine, and pharmaceutically acceptable salts thereof.

Examples of suitable alpha adrenoceptor blockers for use in combination with the pharmaceutical compositions of the present application include tamuslosin, alfuzosin, and silodosin.

Examples of suitable 5-alpha reductase inhibitors for use in combination with the pharmaceutical compositions of the present application include finasteride, dutaseteride and pharmaceutically acceptable salts thereof.

Examples of suitable phosphodiesterase-5 inhibitors for use in combination with the pharmaceutical compositions of the present application include sildenafil, tadalafil, vardenafil, udenafil, avanafil and pharmaceutically acceptable salts thereof.

Examples of suitable therapeutics for obesity: orlistat (Xenical®), lorcaserin (Belviq®), phentermine and topiramate (Qsymia®), buproprion and naltrexone (Contrave®), and uncertain mimetics such as liraglutide (Saxenda®).

Examples of suitable therapeutics for diabetes: metformin, sulfonylureas (DiaBeta®, Glynase®), glipizide (Glucotrol®) glimepiride (Amaryl®), meglitinides, repaglinide (Prandin®), nateglinide (Starlix®), thiazolidinedione (Actos®, Avandia®), DPP-4 inhibitors, sitagliptin (Januvia®), saxagliptin (Onglyza®), linagliptin (Tradjenta®), puringerics, GLP-1 receptor agonists exenatide (Byetta®), liraglutide (Victoza®), SGLT2 inhibitors, canagliflozin (Invokana®), dapagliflozin (Farxiga®) and insulin.

Examples of suitable therapeutics for heart failure: angiotensin-converting enzyme (ACE) inhibitors, enalapril, lisinopril, angiotensin II receptor blockers, (Losartan®), (Valsartan®) beta blockers (Carvedilol®) metoprolol, bisoprolol, diuretics, hydrochlorthiazide, furosemide, aldosterone antagonists, spironolactone, eplerenone (Inspra®), inotropes and digoxin Examples of suitable therapeutics for IBS: alosetron (Lotronex®), lubiprostone (Amitiza®), eluxadoline (Viberzi®), llinaclotide (Linzess®), rifaximin (Xifaxan®), fiber supplements (OTC), psyllium (Metamucil®), methylcellulose (Citrucel®), anti-diarrheal medications, loperamide (Imodium®) bile acid binders, cholestyramine (Prevalite®), colestipol (Colestid®), colesevelam (Welchol®), anticholinergic and antispasmodic medications, (Levsin®) and dicyclomine (Bentyl®).

Examples of suitable therapeutics for preterm labor: tocolytics, magnesium sulfate, corticosteroids, terbutaline, ritodrine, nifedipine, oxytocin receptor antagonists (Atosiban®).

Examples of suitable therapeutics for anxiety: escitalopram (Lexapro®), duloxetine (Cymbalta®), venlafaxine (Effexor XR®) and paroxetine (Paxil®), buspirone benzodiazepines alprazolam (Xanax®), diazepam (Valium®) and lorazepam)(Ativan®).

Examples of suitable therapeutics for depression: selective serotonin reuptake inhibitors (SSRIs), fluoxetine (Prozac®), paroxetine (Paxil®, Pexeva®), sertraline (Zoloft®), citalopram (Celexa®), escitalopram (Lexapro®), serotonin-norepinephrine reuptake inhibitors (SNRIs), duloxetine (Cymbalta®), venlafaxine (Effexor XR®), desvenlafaxine (Pristiq®, Khedezla®), levomilnacipran (Fetzima®), norepinephrine-dopamine reuptake inhibitors (NDRIs), bupropion (Wellbutrin®, Aplenzin®, Forfivo XL®), atypical antidepressants, trazodone and mirtazapine (Remeron®), vortioxetine (Brintellix®), vilazodone (Viibryd®), vilazodone, tricyclic antidepressants, imipramine (Tofranil®) nortriptyline (Pamelor®), amitriptyline, doxepin, trimipramine (Surmontil® desipramine (Norpramin®), protriptyline (Vivactil®), monoamine oxidase inhibitors (MAOIs), tranylcypromine (Parnate®), phenelzine (Nardil®) and isocarboxazid (Marplan®).

In one embodiment, the present application describes a method for treating LUTS, obesity, type 2 diabetes, heart failure, irritable bowel syndrome and similar gastrointestinal disorders, pre-term labor, depression and anxiety, comprising: administering a pharmaceutical composition for the delivery of solabegron, comprising: an immediate release composition, comprising solabegron and at least one pharmaceutically acceptable carrier or diluent; and a modified release composition, comprising solabegron and at least one pharmaceutically acceptable carrier or diluent to a patient in need thereof. Further embodiments describe methods, wherein the patient achieves a blood plasma $C_{max}$ of about 0.5 µg/ml to about 3.5 µg/ml in about 0.75 to about 4 hours after administration. Further embodiments describe methods, wherein the patient achieves a blood plasma $C_{min}$ from about 0.25 µg/ml to about 1.5 µg/ml in about 4 to about 8 hours after administration. Further embodiments describe methods, wherein the patient achieves a blood plasma $C_{min}$ of about 1.5 µg/ml to about 4 µg/ml in about 2 to about 8 hours after the first $C_{min}$. Further embodiments describe methods, wherein the patient achieves a blood plasma $C_{min}$ from about 0.01 µg/ml to about 1.0 µg/ml before about 24 hours after administration. Further embodiments describe methods, further comprising administering one or more additional therapeutic agents or treatments useful for the treatment of LUTS, obesity, type 2 diabetes, heart failure, irritable bowel syndrome and similar gastrointestinal disorders, pre-term labor, depression and anxiety, wherein the one more additional therapeutic agents or treatments are selected from the groups consisting of: antimuscarinic agents; alpha adrenoceptor blockers; botulinum toxin; purinergics; cannabinoids; transient receptor potential (TRP) protein inhibitors; prostaglandins; percutaneous tibial nerve stimulation; 5-alpha reductase inhibitors; and phosphodiesterase-5 inhibitors. Further embodiments describe method, wherein the one or more additional therapeutic agents may be administered prior to, simultaneously with, or following the administration of the pharmaceutical composition comprising solabegron. Further embodiments describe methods, wherein the pharmaceutical composition is administered once a day to a patient in need thereof.

In one embodiment, the present application describes a method for treating LUTS, obesity, type 2 diabetes, heart failure, irritable bowel syndrome and similar gastrointestinal disorders, pre-term labor, depression and anxiety, comprising: administering a pharmaceutical composition, comprising a therapeutically effective amount of solabegron, wherein the pharmaceutical composition releases at least two releases of solabegron, wherein a first release of solabegron achieves a first target $C_{max}$, a second release of solabegron achieves a second target $C_{max}$, a first target $C_{min}$ is achieved between the first release and the second release and a second $C_{min}$ is achieved after the second release. Further embodiments describe methods, wherein said first target $C_{max}$ is about 0.5 µg/ml to about 3.5 µg/ml. Further embodiments describe methods, wherein said second target $C_{max}$ is about 1.5 µg/ml to about 4 µg/ml. Further embodiments describe methods, wherein said first $C_{min}$ is about 0.25 µg/ml to about 1.5 µg/ml. Further embodiments describe methods, wherein said second $C_{min}$ is about 0.01 µg/ml to about 1.0 µg/ml. Further embodiments describe methods, further comprising administering one or more additional therapeutic agents or treatments useful for the treatment of LUTS, obesity, type 2 diabetes, heart failure, irritable bowel syndrome and similar gastrointestinal disorders, pre-term labor, depression and anxiety, wherein the one more additional therapeutic agents or treatments are selected from the groups consisting of: antimuscarinic agents; alpha adrenoceptor blockers; botulinum toxin; purinergics; cannabinoids; transient receptor potential (TRP) protein inhibitors; prostaglandins; percutaneous tibial nerve stimulation; 5-alpha reductase inhibitors; and phosphodiesterase-5 inhibitors. Further embodiments describe methods, wherein the one or more additional therapeutic agents may be administered prior to, simultaneously with, or following the administration of the pharmaceutical composition comprising solabegron. Further embodiments describe methods, wherein the pharmaceutical composition is administered once a day to a patient in need thereof.

In one embodiment the present application describes a method for treating LUTS, obesity, type 2 diabetes, heart failure, irritable bowel syndrome and similar gastrointestinal disorders, pre-term labor, depression and anxiety, comprising: administering a pharmaceutical composition for the delivery of solabegron, comprising: an immediate release composition, comprising solabegron and at least one pharmaceutically acceptable carrier or diluent; and a modified release composition, comprising solabegron and at least one pharmaceutically acceptable carrier or diluent to a patient in need thereof. Additional embodiments describe methods, wherein the patient achieves a blood plasma $C_{max}$ of about 1.5 µg/ml to about 4 µg/ml in about 1 to about 3 hours after administration. Further embodiments describe methods, wherein the patient achieves a blood plasma $C_{min}$ from about 0.5 µg/ml to about 1.5 µg/ml in about 3 to about 5 hours after administration. Still further embodiments describe methods, wherein the patient achieves a blood plasma $C_{max}$ of about 1.5 µg/ml to about 4 µg/ml in about 5 to about 11 hours after administration. Additional embodiments describe methods, wherein the patient achieves a blood plasma $C_{min}$ less than about 0.5 µg/ml after about 12 hours after administration. Still additional embodiments describe methods, wherein the pharmaceutical composition is administered every other day (QOD), once a day (QD), twice a day (BID) or three times a day (TID) to a patient in need thereof. Still other embodiments of the present application describe pharmaceutical compositions, further comprising one or more additional therapeutic agents or treatments useful for the treatment of LUTS, obesity, type 2 diabetes, heart failure, irritable bowel syndrome and similar gastrointestinal disorders, pre-term labor, depression and anxiety, wherein the one more additional therapeutic agents or treatments are antimuscarinic agents, alpha adrenoceptor blockers, botulinum toxin, purinergics, cannabinoids, transient receptor potential (TRP) protein inhibitors, prostaglandins, 5-alpha reductase inhibitors, phosphodiesterase-5 inhibitors or percutaneous tibial nerve stimulation and the one or more additional therapeutic agents may be administered prior to, simultaneously with, or following the administration of the pharmaceutical composition comprising solabegron.

In one embodiment the present application describes a method for treating LUTS, obesity, type 2 diabetes, heart failure, irritable bowel syndrome and similar gastrointestinal disorders, pre-term labor, depression and anxiety, comprising: administering a pharmaceutical composition, comprising a therapeutically effective amount of solabegron, wherein the pharmaceutical composition releases at least two releases of solabegron, wherein a first release of solabegron achieves a first target $C_{max}$, a second release of solabegron achieves a second target $C_{max}$, a first target $C_{min}$ is achieved between the first release and the second release and a second $C_{min}$ is achieved after the second release. Additional embodiments describe methods, wherein said first target $C_{max}$ is about 1.5 µg/ml to about 4 µg/ml, said second target $C_{max}$ is about 1.5 µg·ml to about 4 µg/ml, said first $C_{min}$ is about 0.5 µg/ml to about 1.5 µg/ml and said second $C_{min}$ is about 0.01 µg/ml to about 0.5 µg/ml. Still other embodiments of the present application describe pharmaceutical compositions, further comprising one or more additional therapeutic agents or treatments useful for the treatment of LUTS, obesity, type 2 diabetes, heart failure, irritable bowel syndrome and similar gastrointestinal disorders, pre-term labor, depression and anxiety, wherein the one more additional therapeutic agents or treatments are antimuscarinic agents, alpha adrenoceptor blockers, botulinum toxin, purinergics, cannabinoids, transient receptor potential (TRP) protein inhibitors, prostaglandins, 5-alpha reductase inhibitors, phosphodiesterase-5 inhibitors or percutaneous tibial nerve stimulation and the one or more additional therapeutic agents may be administered prior to, simultaneously with, or following the administration of the pharmaceutical composition comprising solabegron. Still further embodiments describe methods, wherein the pharmaceutical composition is administered every other day (QOD), once a day (QD), twice a day (BID) or three times a day (TID) to a patient in need thereof.

In one embodiment the present application describes a method of treating one or more symptoms of OAB, comprising: administering a pharmaceutical composition, comprising a therapeutically effective amount of solabegron and at least one pharmaceutically acceptable diluent or carrier, wherein the one or more symptoms of OAB are selected from the group consisting of: frequency of urinary urgency; nocturia; increase in urinary micturition frequency; and urinary incontinence. Further embodiments describe methods, wherein the pharmaceutical composition may be administered in the morning or the pharmaceutical composition may be administered with a meal. Additional embodiments describe methods, wherein the improvement in the one or more symptoms of over active bladder is increased bladder volume as measured by void volume.

In one embodiment, the present application describes a once-daily treatment for LUTS, obesity, type 2 diabetes, heart failure, irritable bowel syndrome and similar gastrointestinal disorders, pre-term labor, depression and anxiety that achieves a desired blood plasma $C_{max}$ while also not desensitizing the beta-3 adrenoceptor, comprising: a pharmaceutical composition, comprising a therapeutically effective amount of solabegron, wherein the pharmaceutical composition releases at least two releases of solabegron, wherein a first release of solabegron achieves a first target $C_{max}$, a second release of solabegron achieves a second target $C_{max}$, a first target $C_{min}$ is achieved between the first release and the second release and a second $C_{min}$ is achieved after the second release. Further embodiments describe once-daily treatments, wherein said first target $C_{max}$ is about 0.5 µg/ml to about 3.5 µg/ml. Further embodiments describe once-daily treatments, wherein said second target $C_{max}$ is about 1.5 µg·ml to about 4 µg/ml, wherein said first $C_{min}$ is about 0.25 µg/ml to about 1.5 µg/ml. Further embodiments describe once-daily treatments, wherein said second $C_{min}$ is from about 0.01 µg/ml to about 1.0 µg/ml. Further embodiments describe once-daily treatments, further comprising administering one or more additional therapeutic agents or treatments useful for the treatment of LUTS, obesity, type 2 diabetes, heart failure, irritable bowel syndrome and similar gastrointestinal disorders, pre-term labor, depression and anxiety, wherein the one more additional therapeutic agents or treatments are selected from the groups consisting of: antimuscarinic agents; alpha adrenoceptor blockers; botulinum toxin; purinergics; cannabinoids; transient receptor potential (TRP) protein inhibitors; prostaglandins; percutaneous tibial nerve stimulation; 5-alpha reductase inhibitors; and phosphodiesterase-5 inhibitors. Further embodiments describe once-daily treatments, wherein the one or more additional therapeutic agents may be administered prior to, simultaneously with, or following the administration of the pharmaceutical composition comprising solabegron.

In one embodiment, the present application describes a once-daily treatment for LUTS, obesity, type 2 diabetes, heart failure, irritable bowel syndrome and similar gastrointestinal disorders, pre-term labor, depression and anxiety that achieves a desired blood plasma $C_{max}$ while also not desensitizing the beta-3 adrenoceptor, comprising: at least one immediate release composition, comprising solabegron and at least one pharmaceutically acceptable carrier or diluent; and at least one modified release composition, comprising solabegron and at least one pharmaceutically acceptable carrier or diluent. Further embodiments describe once-daily treatments, wherein the at least one immediate release composition comprises about 75 mg to about 250 mg solabegron. Further embodiments describe once-daily treatments, wherein the at least one modified release composition comprises about 100 mg to about 400 mg solabegron. Further embodiments describe once-daily treatments, wherein the at least one immediate release composition achieves a blood plasma $C_{max}$ in about 0.75 to about 4 hours after administration to a patient in need of treatment. Further embodiments describe once-daily treatments, wherein the at least one modified release composition achieves a blood plasma $C_{max}$ in about 2 to about 8 hours after the first $C_{min}$. Further embodiments describe once-daily treatments, further comprising administering one or more additional therapeutic agents or treatments useful for the treatment of LUTS, obesity, type 2 diabetes, heart failure, irritable bowel syndrome and similar gastrointestinal disorders, pre-term labor, depression and anxiety, wherein the one more additional therapeutic agents or treatments are selected from the groups consisting of: antimuscarinic agents; alpha adrenoceptor blockers; botulinum toxin; purinergics; cannabinoids; transient receptor potential (TRP) protein inhibitors; prostaglandins; percutaneous tibial nerve stimulation; 5-alpha reductase inhibitors; and phosphodiesterase-5 inhibitors. Further embodiments describe once-daily treatments, wherein the one or more additional therapeutic agents may be administered prior to, simultaneously with, or following the administration of the pharmaceutical composition comprising solabegron.

In one embodiment the present application describes a once-daily treatment for LUTS, obesity, type 2 diabetes, heart failure, irritable bowel syndrome and similar gastrointestinal disorders, pre-term labor, depression and anxiety that achieves a desired blood plasma $C_{max}$ while also not desensitizing the beta-3 adrenoceptor or the biochemical pathways leading to the functional response, comprising: a pharmaceutical composition, comprising a therapeutically effective amount of solabegron, wherein the pharmaceutical composition releases at least two releases of solabegron, wherein a first release of solabegron achieves a first target $C_{max}$, a second release of solabegron achieves a second target $C_{max}$, a first target $C_{min}$ is achieved between the first release and the second release and a second $C_{min}$ is achieved after the second release. Additional embodiments describe treatments, wherein said first target $C_{max}$ is about 1.5 µg/ml to about 4 µg/ml, said second target $C_{max}$ is about 1.5 µg·ml to about 4 µg/ml, said first $C_{min}$ is about 0.5 µg/ml to about 1.5 µg/ml and said second $C_{min}$ is about 0.01 µg/ml to about 0.5 µg/ml. Further embodiments describe treatments further comprising administering one or more additional therapeutic agents useful for the treatment of LUTS, obesity, type 2 diabetes, heart failure, irritable bowel syndrome and similar gastrointestinal disorders, pre-term labor, depression and anxiety, wherein the one more additional therapeutic agents are selected from the groups consisting of: antimuscarinic agents; alpha adrenoceptor blockers; 5-alpha reductase inhibitors; and phosphodiesterase-5 inhibitors, wherein the one or more additional therapeutic agents may be administered prior to, simultaneously with, or following the administration of the pharmaceutical composition comprising solabegron.

In one embodiment the present application describes a once-daily treatment for LUTS, obesity, type 2 diabetes, heart failure, irritable bowel syndrome and similar gastrointestinal disorders, pre-term labor, depression and anxiety that achieves a desired blood plasma $C_{max}$ while also not desensitizing the beta-3 adrenoceptor, comprising: at least one immediate release composition, comprising solabegron and at least one pharmaceutically acceptable carrier or diluent; and at least one modified release composition, comprising solabegron and at least one pharmaceutically acceptable carrier or diluent. Additional embodiments describe treatments, wherein the at least one immediate release composition comprises about 100 mg to about 300 mg solabegron and the at least one modified release composition comprises about 100 mg to about 300 mg solabegron. Further embodiments describe treatments, wherein the at least one immediate release composition achieves a blood plasma $C_{max}$ in about 1 to about 3 hours after administration to a patient in need of treatment and the at least one modified release composition achieves a blood plasma $C_{max}$ in about 5 to about 11 hours after administration to a patient in need of treatment. Still further embodiments describe treatments, further comprising administering one or more additional therapeutic agents useful for the treatment of LUTS, obesity, type 2 diabetes, heart failure, irritable bowel syndrome and similar gastrointestinal disorders, pre-term labor, depression and anxiety, wherein the one more additional therapeutic agents are selected from the groups consisting of: antimuscarinic agents; alpha adrenoceptor blockers; 5-alpha reductase inhibitors; and phosphodiesterase-5 inhibitors, wherein the one or more additional therapeutic agents may be administered prior to, simultaneously with, or following the administration of the pharmaceutical composition comprising solabegron.

EXAMPLES

HEK cells transfected with the human beta-3 adrenoceptor according to the method of Vrygag et al (2009) will be employed. Additional cell lines, such as CHO, SK-N-MC neuroblastoma cells or cultured human adipocytes may be considered.

For the desensitization experiments, the cells will be cultured for 0.5 hr to 24 hr in a serum-free medium in the presence of vehicle or a concentration of 0.01 to 10-µM beta-3 adrenoceptor agonists. Beta-3 agonists that may be studied include solabegron, CL 316,243 or isoproterenol. Cells will be washed with serum-free medium for a period of 1 to 4 hr.

Example 1: Cyclic AMP Accumulation or ERK Activation Endpoint Assessment of Beta-3 Adrenoceptor Desensitization Cells will be detached from the surface using enzyme-free cell dissociation buffer and washed once with Hank's balanced salt solution (HBSS). Cells will be re-suspended in HBSS supplemented with 5 mM HEPES and 0.05% bovine serum albumin. The cells will be stimulated with the appropriate concentration-response to a beta-3 adrenoceptor agonist or vehicle. The stimulation mixture will contain the cAMP phosphodiesterase inhibitors IBMX and RO 20-1724 (100 µM each). Cells will be added to the stimulation mixture 1:1 in a 384 well optiplate and stimulated for 30 min at room temperature. cAMP detection will be using a LANCE® cAMP Kit (PerkinElmer). ERK activation will be measured by ELISA. Desensitization at the level of adenylyl cyclase will be confirmed by measuring the response to forkolin.

Example 2: Radioligand-Binding Studies Endpoint Assessment of Beta-3 Adrenoceptor Desensitization

[$^3$H]-L 748,337 saturation radioligand binding will be performed as previously described (van Wieringen et al. 2011). Briefly, cells at approximately 80% confluence will be washed with PBS, harvested by scraping the culture flasks with a cell scraper, washed twice by centrifugation, and then homogenized in ice-cold buffer (50 mM Tris, 0.5 mM EDTA, pH 7.5). The homogenates will be centrifuged for 20 min at 50,000×g at 4° C. The pellets will be resuspended in buffer and stored at −80° C. Aliquots of the respective membrane preparation (approximately 50-100 µg protein/assay) will be incubated in a total volume of 250 µl of binding buffer (10 mM Tris, 0.9 mN NaCl at pH 7.4) at 25° C. for 60 min. Non-specific binding will be defined using 100 µM isoproterenol. In saturation experiments, eight radioligand concentrations will be used. All experiments will be performed in duplicates in 96 well plates, and incubations will be terminated by rapid vacuum filtration.

Each filter will be washed with approximately 2-3 ml of ice-cold buffer. Radioactivity adherent to the filters will be quantified in Perkin Elmer scintillator counter.

Example 3: Alteration in G-Protein Expression Endpoint Assessment of Beta-3 Receptor Desensitization Cells treated with beta-3 agonists at various time-points will be washed with PBS, harvested, homogenized and centrifuged. The pellets will be re-homogenized, boiled loaded on to SDS gels and electrophoresed for approximately 1 hr at 40 mA. Primary antibodies (rabbit polyclonal) for detection of G protein subunits ($G_S$, Gi1, Gi2, Gi3, Gq/11) will be used. Immunoblotting will be performed for approximately 12 hr at 4° C. Following washing, a secondary antibody (i.e. donkey anti-rabbit coupled to horseradish peroxidase) will be used. Luminescence signals will be detected and quantified.

Example 4: Prevention of Receptor Desensitization

Macroscopically normal bladders obtained from Male CD rats (220-250 g) were used. Furthermore, tissues were rejected if they did not respond adequately to viability checks. Each bladder was cleaned free of surrounding connective tissue and halved longitudinally. The bladder longitudinal smooth muscle, with the urothelium still attached were mounted in 25 ml organ baths containing physiological saline solution (PSS) (composition: 119.0 mM NaCl, 4.7 mM KCl, 1.2 mM $MgSO_4$, 24.9 mM $NaHCO_3$, 1.2 mM $KH_2PO_4$, 2.5 mM $CaCl_2$ and 11.1 mM glucose) supplemented with 1 μM prazosin ($α_1$-adrenoceptor antagonist) and 30 nM ICI118551 ($β_2$-adrenoceptor antagonist), aerated with 95% $O_2$/5% $CO_2$ gas mix, warmed and maintained at approximately 37° C. throughout the experiment. Changes in force production were recorded using transducers. After mounting, the bladder halves were allowed to equilibrate for at least 30 min before they were set to a stable tension of approximately 1.0 g. The tissue was then allowed to equilibrate over at least a 60 min period with washes every 15 min.

It is envisioned that the above studies performed in rat bladder tissue could also be performed in human bladder tissue.

EFS Parameters and Viability Check

In initial experiments the parameters for the EFS were assessed by performing a frequency curve to determine a frequency that would give a response that was approximately 80% of the response seen to 80 mM KCl. Optimal EFS parameters were determined to be: 30 Volts, square pulse of 0.1 ms, train of 4 seconds every 120 seconds, 15 Hz. This frequency was then used to stimulate the tissue for all subsequent experiments. The viability of bladder strips was tested by stimulating the tissue with EFS for minimum of ten minutes. Tissues that failed to produce a response of at least 1.0 g were rejected.

Experimental Protocol

Pilot studies to determine $EC_{90}$ concentrations of the test compounds were performed. Upon stabilization of the baseline tension, the bladder muscle strips were stimulated with EFS parameters described above. The resulting contractile responses were allowed to stabilize before adding cumulative concentrations of test compound (half-log increments) in a cumulative concentration response curve (CCRC). A vehicle and a positive control (CL-316,243) were run in the same manner in order to compare with the test compounds. From the data obtained in these experiments, $EC_{90}$ concentrations of the test compounds were determined for use in subsequent experiments.

The bladder muscle strips were incubated with the $EC_{90}$ determined for each test compound in the pilot studies, for a period of 1 or 3 hr. Following compound incubation, the tissues were washed with PSS for a period of 1, 3 or 6 hr, with washes approximately every 15 min, to remove the drug. At the end of the final wash period the tissues were stimulated with EFS, and left to equilibrate for at least 30 min. A CCRC was then performed in each tissue. Tissue responses were calculated as the mean (SEM) and expressed as percentage of EFS induced tone.

Determination of $EC_{90}$ Concentration for Beta-3 Adrenoceptor Agonists to Inhibit EFS-Induced Contraction in Rat Isolated Bladder In the initial pilot experiments, concentration response curves were performed to the test compounds to determine an $EC_{90}$ value for use in later experiments. The calculated values for CL-316,243 and solabegron were 0.042 and 1.0 μM, respectively.

Effect of the Washout Period Following a One Hr Incubation with Test Compound

Tissues were incubated with the $EC_{90}$ concentration of the test compounds for one hr followed by one hr, three hr or six hr of washing with PSS. After only one hr of washing, the response to solabegron was significantly attenuated (FIG. 2). Responses to higher concentrations of solabegron were also significantly attenuated after three hr of washing. After six hr of washing the response to solabegron was similar to that seen in tissues that had not been pre-exposed to the test compound (FIG. 2). This EFS-induced potentiation of bladder contraction from baseline was not observed with solabegron. These data suggest that incubation of the rat bladder with beta-3 adrenoceptor agonists produced marked receptor desensitization, and that the receptor is re-sensitized in a time-dependent manner following removal of the agonist by removing the ligand by washing out.

Effect of the Washout Period Following a Three Hr Incubation with Test Compound.

In the next series of experiments, tissues were incubated with the $EC_{90}$ concentration of the test compounds for three hr followed by either one hr, three hr or six hr of washing with PSS.

After only one hr of washing, the responses to solabegron and CL-316,243 were significantly attenuated (FIGS. 3 AND 4). Responses to the highest concentrations of solabegron were also significantly attenuated after three hr of washing. After six hr of washing the responses to solabegron or the tool compound CL-316,243 were similar to that seen in tissues which had not been pre-exposed to the test compound (FIGS. 3 AND 4).

CONCLUSIONS

The data in the present experiments demonstrate that prolonged administration of beta-3 adrenoceptor agonists produce time-dependent desensitization of the beta-3 adrenoceptor in the rat bladder. Recovery of receptor desensitization was achieved by removal or washing-out the agonist from the tissue, such that the receptor-mediated functional response in the bladder returns to vehicle-treated or baseline conditions.

Following either a one hr or three hr incubation with the $EC_{90}$ concentration of solabegron, the ability of solabegron to reduce the magnitude of EFS-mediated responses in rat bladder muscle was still attenuated markedly when the tissue was washed for only one or three hr. After 6 hr of washing post-incubation, the ability of solabegron to reduce EFS was not significantly different than that seen in muscle strips that had only been exposed to an equivalent volume of vehicle and not to solabegron. These data indicate that the effects of the exposure of the tissue to an $EC_{90}$ concentration of solabegron produced desensitization of the responses mediated by the beta-3 adrenoceptor. The $EC_{90}$ concentration of the beta-3 adrenoceptor agonists used in this study was selected because it reflects a clinically relevant concentration comparable to the Cmax observed in patients. Beta-3 receptor desensitization appeared to occur rapidly, as only 1 hr incubation was necessary to produce marked inhibition of the beta-3 receptor mediated response.

The re-sensitization response occurred in a time-dependent manner, indicating the functional defect in the tissue was reversible, and recovery was completed within 6 hr. Such a time course of desensitization and re-sensitization is consistent with the time course that will be used for a pulsatile formulation administration of solabegron in patients.

CL-316,243 was used as a reference standard as a rodent selective beta-3 adrenoceptor agonist. Attenuation in the ability of CL-316,243 to reduce the magnitude of EFS responses in rat bladder muscle tissue was also seen after a three hr pre-incubation to the $EC_{90}$ concentration of CL-316, 243. Following washout of CL-316,243 the recovery of the beta-3 adrenoceptor mediated response occurred in a time-dependent manner, as was seen with solabegron.

In conclusion, the data in the present experiments demonstrate that prolonged administration of beta-3 adrenoceptor agonists can produce time-dependent desensitization of the beta-3 adrenoceptor-mediated responses in the rat bladder. Recovery of receptor desensitization and prevention of prolonged receptor desensitization can be achieved by removal of the agonist from the tissue, such that the receptor-mediated functional response returns to baseline conditions. Beta-3 receptor desensitization can be prevented by giving sufficient time between drug exposures for the tissue to recover. Therefore, prevention of prolonged administration of a beta-3 adrenoceptor agonist in patients with OAB may be desirable in order to preserve and increase therapeutic efficacy. Thus, the daily administration of a beta-3 adrenoceptor agonist that is formulated to occur in a pulsatile manner may be the viable approach for chronic treatment. Such an approach will reduce beta-3 adrenoceptor desensitization and promote recovery of desensitized receptors to become active.

Example 5: Multiparticulate Formulation for the Release of Solabegron

A formulation utilizing solabegron is proposed, wherein pellets containing solabegron will form the basis for multiple releases of solabegron to a patient in need. The formulation will contain at least two populations of pellets, wherein at least one population comprises an immediate release population and at least one population comprises a modified (i.e. sustained and/or delayed) release population. The immediate release pellets will release solabegron immediately in the GI tract, whereas the modified release pellets will release solabegron at a later time inside the GI tract. The modified release pellets may be coated with either a pH dependent (enteric) coating or a time dependent coating so as to delay the second release of solabegron to the desired position in the GI tract. Both types of pellets may contain any physical form of solabegron such as, for example, amorphous or crystalline solid. The pellets may be drug-layered pellets or matrix-type pellets.

Example 6: Drug Coated Spheres/Pellet with an Inert Core for the Release of Solabegron A formulation utilizing solabegron is proposed, wherein spheres/pellets with an inert core containing solabegron will form the basis for multiple releases of solabegron to a patient in need. The formulation will contain at least two populations of spheres/pellets with an inert core, wherein at least one population comprises an immediate release population and at least one population comprises a modified (i.e. sustained and/or delayed) release population. The immediate spheres/pellets with an inert core will release solabegron immediately in the GI tract, wherein the modified release spheres/pellets with an inert core will release solabegron at a later time inside the GI tract. The modified release spheres/pellets with an inert core may be coated with either a pH dependent (enteric) coating or a time dependent coating so as to delay the second release of solabegron to the desired position in the GI tract. Both types of spheres/pellets with an inert core may contain any physical form of solabegron such as, for example, amorphous or crystalline solid.

Example 7: Bi-Layer Tablet for the Release of Solabegron

A formulation utilizing solabegron is proposed, wherein a bi-layer tablet containing solabegron will form the basis for the multiple releases of solabegron to a patient in need. The formulation will contain a tablet having both an immediate release layer and a modified release layer. The immediate layer will release solabegron immediately in the GI tract, whereas the modified release layer will release solabegron at a later time inside the GI tract. The modified release layer may be coated with either a pH dependent (enteric) coating or a time dependent coating so as to delay the second release of solabegron to the desired position in the GI tract. Both types of layers may contain any physical form of solabegron such as, for example, amorphous or crystalline solid.

Example 8: Matrix Tablet for the Release of Solabegron

A formulation utilizing solabegron is proposed, wherein a matrix tablet containing solabegron will form the basis for the multiple releases of solabegron to a patient in need thereof. The formulation will contain a well-mixed composite of drug(s) with rate-controlling excipients. Numerous sustained and/or delayed release tablets such as membrane controlled system, matrices with water soluble/insoluble polymers, and osmotic systems may be utilized. The tablet may contain either the amorphous form of solabegron or the crystalline form. The delayed/sustained release can be achieved by applying a permeable or semipermeable membrane to the tablet core or by mixing the drug with excipient that is either a hydrophilic polymer with high viscosity and gel forming capability or a hydrophobic excipient that slows down the diffusion of drug molecule. An immediate release drug layer can be coated to the tablet that will be available for an early release in the GI tract, while the delayed release core will be designed to delay the drug release after a time period in a designed region of the GI tract.

Example 9: Multicore Tablet for the Release of Solabegron

A formulation utilizing solabegron is proposed, wherein a multicore tablet containing solabegron will form the basis for the multiple releases of solabegron to a patient in need thereof. The formulation will contain a multicore tablet that comprises multiple discrete cores consisting of at least one immediate release core and at least one delayed/sustained release core contained within the same tablet. The at least one immediate release core will be available for an early release in the GI tract, while the at least one delayed/sustained release core will be designed to delay the drug release after a time period in a designed region of the GI tract.

Example 10: Gastroretentive Delivery System for the Release of Solabegron

A formulation utilizing solabegron is proposed, wherein a gastroretentive oral dosage form containing solabegron will form the basis for the multiple releases of solabegron to a patient in need. The formulation will contain a tablet or capsule having both an immediate release and modified release component. The immediate layer will release solabegron immediately in the GI tract, wherein the modified release layer will release solabegron at a later time inside the GI tract. The gastroretentive oral dosage form may utilize mucoadhesive, swellable, high density or floating technologies to prolong residence time in the stomach thereby allowing a prolonged period for release of both first and second releases in the stomach or upper GI. Both releases may contain any physical form of solabegron such as, for example, amorphous or crystalline solid.

Example 11: Proposed Formulations for the Release of Solabegron

It is proposed that solabegron be formulated as a once-daily formulation having two distinct release components. It is envisioned that such formulations may exist wherein both the two release components contain the same or different amounts of solabegron and when different either the first or second release may contain the greater amount of solabegron. Provided below in TABLE 1 are formulations that should provide a therapeutic amount of solabegron to a patient in need without desensitizing the beta-3 adrenoceptor.

TABLE 1

|  | Low Dose | High Dose | Mixed Dose |
|---|---|---|---|
| $C_{max}$ 1 (hours after administration) | 0.75-4.0 | 0.75-4.0 | 0.75-4.0 |
| $C_{min}$ 1 (hours after administration) | 4.0-8.0 | 4.0-8.0 | 4.0-8.0 |
| $C_{max}$ 2 (hours after $C_{min}$ 1) | 2.0-8.0 | 2.0-8.0 | 2.0-8.0 |
| $C_{min}$ 2 (hours after administration) | 24 | 24 | 24 |
| Time Between $C_{max}$ 1 and $C_{max}$ 2 (hours) | 2.0-8.0 | 2.0-8.0 | 2.0-8.0 |
| $C_{max}$ 1 (µg/ml) | 0.5-2 | 1.5-3.5 | 0.5-2 |
| $C_{max}$ 2 (µg/ml) | 1.5-3 | 2.5-4 | 2.5-4 |
| $C_{min}$ 1 (µg/ml) | 0.25-1.0 | 0.5-1.5 | 0.25-1.0 |
| $C_{min}$ 2 (µg/ml) | 0.01-1 | 0.25-1 | 0.01-1 |

TABLE 1-continued

|  | Low Dose | High Dose | Mixed Dose |
|---|---|---|---|
| First Release | 75-250 | 75-250 | 75-250 |
| Second Release | 100-400 | 100-400 | 100-400 |
| Time at or below 1.0 µg/ml over a 24 hour period (hours) | about 6 to about 9 | about 6 to about 9 | about 6 to about 9 |

Although the present disclosure has been described in considerable detail with reference to certain preferred versions thereof, other versions are possible. Therefore, the spirit and scope of the application should not be limited to the description of the preferred versions described herein.

All features disclosed in the specification, including the abstract and drawings, and all the steps in any method or process disclosed, may be combined in any combination, except combinations where at least some of such features and/or steps are mutually exclusive. Each feature disclosed in the specification, including abstract and drawings, can be replaced by alternative features serving the same, equivalent or similar purpose, unless expressly stated otherwise. Thus, unless expressly stated otherwise, each feature disclosed is one example only of a generic series of equivalent or similar features. Various modifications of the application, in addition to those described herein, will be apparent to those skilled in the art from the foregoing description. Such modifications are also intended to fall within the scope of the appended claims.

Throughout the above specification a number of references have been cited and or referred to it is to be understood that unless specifically noted, all references cited in the above specification and or referred to in the above specification are hereby incorporated by reference in their entirety.

What is claimed is:

1. A method for treating LUTS in a patient in need thereof, comprising: administering once a day to the patient a pharmaceutical composition for the delivery of a therapeutically effective amount of solabegron, comprising: an immediate release composition, comprising solabegron and at least one pharmaceutically acceptable carrier or diluent; and a delayed release composition, comprising solabegron and at least one pharmaceutically acceptable carrier or diluent to the patient, wherein the immediate release composition achieves a first plasma $C_{max}$, the delayed release composition achieves a second plasma $C_{max}$, a first plasma $C_{min}$ is achieved after the first plasma $C_{max}$ and before the second plasma $C_{max}$ and a second plasma $C_{min}$ is achieved after the second plasma $C_{max}$; wherein the first plasma $C_{max}$ is about 0.5 ug/ml to about 4.0 ug/ml in about 0.75 to about 4 hours after administration of the pharmaceutical composition; wherein the first plasma $C_{min}$ is about 0.25 ug/ml to about 1.5 ul/ml in about 4 to about 8 hours after administration of the pharmaceutical composition; wherein the second plasma $C_{max}$ is about 0.5 ug/ml to about 4 ug/ml in about 2 to about 8 hours after the first plasma $C_{min}$; wherein the second plasma $C_{min}$ is about 0.01 ug/ml to about 1.0 ug/ml before about 24 hours after administration of the pharmaceutical composition; wherein the pharmaceutical composition reduces desensitization of the beta-3 adrenoceptor, when compared to an immediate release pharmaceutical composition of solabegron administered twice daily.

2. The method according to claim 1, further comprising administering one or more additional therapeutic agents or treatments useful for the treatment of LUTS, wherein the one more additional therapeutic agents or treatments are selected from the groups consisting of: antimuscarinic agents; alpha adrenoceptor blockers; botulinum toxin; purinergics; cannabinoids; transient receptor potential (TRP) protein inhibitors; prostaglandins; percutaneous tibial nerve stimulation; 5-alpha reductase inhibitors; and phosphodiesterase-5 inhibitors.

3. The method according to claim 2, wherein the one or more additional therapeutic agents may be administered prior to, simultaneously with, or following the administration of the pharmaceutical composition comprising solabegron.

4. The method of claim 1, wherein said LUTS is selected from overactive bladder and a prostate disorder.

5. The method of claim 4, wherein treating overactive bladder comprises treating one or more symptoms of OAB selected from the group consisting of: frequency of urinary urgency; nocturia; increase in urinary micturition frequency; and urinary incontinence, voided volume, post-void residual volume and patient reported outcomes.

6. The method of claim 1, wherein the immediate release comprises about 75 mg to about 250 mg of solabegron.

7. The method of claim 1, wherein the delayed release comprises about 100 mg to about 400 mg of solabegron.

8. The method of claim 1, wherein the immediate release comprises 50, 55, 60, 65, 75, 80, 85, 90, 95, 100, 105, 110, 115, 120, 125, 130, 135, 140, 145 or 150 mg of solabegron.

9. The method of claim 1, wherein the delayed release comprises 100, 105, 110, 115, 120, 125, 130, 135, 140, 145, 150, 155, 160, 165, 170, 175, 180, 185, 190, 195, 200, 205, 210, 215, 220, 225, 230, 235, 240, 245, 250, 255, 260, 265, 270, 275, 280, 285, 290, 295, 300, 305, 310, 315, 320, 325, 330, 335, 340, 345 or 350 mg of solabegron.

10. The method of claim 1, wherein the immediate release composition is an immediate release drug layer and the delayed release composition is a delayed release core, wherein the immediate release drug layer is coated on the delayed release core.

11. The method of claim 1, wherein the pharmaceutical composition is a single unit dose.

12. The method according to claim 1, wherein the first plasma $C_{max}$ is about 0.5 µg/ml to about 3.5 µg/ml.

13. The method according to claim 1, wherein the first plasma $C_{max}$ is about 1 µg/ml to about 3.5 µg/ml.

14. The method according to claim 1, wherein the first plasma $C_{max}$ is about 1 µg/ml to about 2 µg/ml.

15. The method according to claim 1, wherein the first plasma $C_{max}$ is about 1.5 µg/ml to about 4 µg/ml.

16. The method according to claim 1, wherein the first plasma $C_{max}$ is about 1.5 µg/ml to about 3.5 µg/ml.

17. The method according to claim 1, wherein the first plasma $C_{max}$ is about 1.5 µg/ml to about 3.0 µg/ml.

18. The method according to claim 1, wherein the first plasma $C_{max}$ is about 2.0 µg/ml to about 3.5 µg/ml.

19. The method according to claim 1, wherein the first plasma $C_{max}$ is about 2.0 µg/ml to about 3.0 µg/ml.

20. The method according to claim 1, wherein the first plasma $C_{max}$ is achieved about 1.5 hours to about 3 hours after administration of the pharmaceutical composition.

21. The method according to claim 1, wherein the first plasma $C_{max}$ is achieved about 1 hours to about 3 hours after administration of the pharmaceutical composition.

22. The method according to claim 1, wherein the first plasma $C_{max}$ is about 1.5 µg/ml to about 4.0 µg/ml.

23. The method according to claim 1, wherein the second plasma $C_{max}$ is about 1.5 µg/ml to about 3.0 µg/ml.

24. The method according to claim 1, wherein the second plasma $C_{max}$ is about 2.5 µg/ml to about 4.0 µg/ml.

25. The method according to claim 1, wherein the second plasma $C_{max}$ is about 2.0 µg/ml to about 4.0 µg/ml.

26. The method according to claim 1, wherein the second plasma $C_{max}$ is about 2.0 µg/ml to about 3.0 µg/ml.

27. The method according to claim 1, wherein the second plasma $C_{max}$ is about 3.0 µg/ml to about 4.0 µg/ml.

28. The method according to claim 1, wherein the second plasma $C_{max}$ is achieved in about 4 to about 6 hours after the first blood plasma $C_{min}$.

29. The method according to claim 1, wherein the second plasma $C_{max}$ is achieved in about 14 to about 16 hours after administration of the pharmaceutical composition.

30. The method according to claim 1, wherein the first plasma $C_{min}$ is from about 0.25 µg/ml to about 1 µg/ml.

31. The method according to claim 1, wherein the first plasma $C_{min}$ is from about 0.5 µg/ml to about 1.5 µg/ml.

32. The method according to claim 1, wherein the first plasma $C_{min}$ is from about 0.5 µg/ml to about 1.0 µg/ml.

33. The method according to claim 1, wherein the first plasma $C_{min}$ is from about 0.75 µg/ml to about 1.5 µg/ml.

34. The method according to claim 1, wherein the first plasma $C_{min}$ is from about 0.25 µg/ml to about 1.25 µs/ml.

35. The method according to claim 1, wherein the first plasma $C_{min}$ is achieved about 5 to about 6 hours after administration of the pharmaceutical composition.

36. The method according to claim 1, wherein the second plasma $C_{min}$ is from about 0.01 µg/ml to about 0.5 µg/ml.

37. The method according to claim 1, wherein the second plasma $C_{min}$ is from about 0.1 µg/ml to about 1.0 µg/ml.

38. The method according to claim 1, wherein the second plasma $C_{min}$ is from about 0.25 µg/ml to about 1.0 µg/ml.

39. The method according to claim 1, wherein the second plasma $C_{min}$ is from about 0.5 µg/ml to about 1.0 µg/ml.

40. The method according to claim 1, wherein the second plasma $C_{min}$ is from about 0.75 µg/ml to about 1.0 µg/ml.

41. The method according to claim 1, wherein the second plasma $C_{min}$ is less than about 0.5 µg/ml.

42. The method according to claim 1, wherein the second plasma $C_{min}$ is achieved before about 20 hours after administration of the pharmaceutical composition.

43. The method according to claim 1, wherein the second plasma $C_{min}$ is achieved before about 16 hours after administration of the pharmaceutical composition.

44. The method according to claim 1, wherein the pharmaceutical composition achieves a plasma concentration of about 1 µg/ml or below for about 6 to about 9 hours during a 24 hour period.

45. The method according to claim 1, wherein the pharmaceutical composition achieves a plasma concentration of about 1 µg/ml or below for about 7 to about 8 hours during a 24 hour period.

46. The method according to claim 1, wherein the pharmaceutical composition achieves a plasma concentration of about 0.5 µg/ml or below for about 12 to about 18 hours.

47. The method according to claim 1, wherein the pharmaceutical composition achieves an area under the curve (AUC) of about 11,000 ng hr/ml to about 30,000 ng hr/ml over a 24 hour period.

48. The method according to claim 1, wherein the time between the first plasma $C_{max}$ and the second blood plasma $C_{max}$ is about 3 hours to about 7 hours.

49. The method according to claim 1, wherein the time between the first plasma $C_{max}$ and the second blood plasma $C_{max}$ is about 4 hours to about 6 hours.

50. The method of claim 1, wherein the immediate release comprises about 30 mg to about 500 mg of solabegron.

51. The method of claim 1, wherein the immediate release comprises about 75 mg to about 400 mg of solabegron.

52. The method of claim 1, wherein the immediate release comprises about 75 mg to about 250 mg of solabegron.

53. The method of claim 1, wherein the immediate release comprises about 100 mg to about 300 mg of solabegron.

54. The method of claim 1, wherein the immediate release comprises about 125 mg of solabegron.

55. The method of claim 1, wherein the immediate release comprises about 200 mg of solabegron.

56. The method of claim 1, wherein the delayed release comprises about 75 mg to about 400 mg of solabegron.

57. The method of claim 1, wherein the delayed release comprises about 100 mg to about 300 mg of solabegron.

58. The method of claim 1, wherein the delayed release comprises about 30 mg to about 500 mg of solabegron.

59. The method of claim 1, wherein the delayed release comprises about 125 mg of solabegron.

60. The method of claim 1, wherein the delayed release comprises about 200 mg of solabegron.

* * * * *